US005646009A

United States Patent [19]
Rhoads et al.

[11] Patent Number: 5,646,009
[45] Date of Patent: Jul. 8, 1997

[54] HYBRID VECTOR AND METHOD RESULTING IN PROTEIN OVERPRODUCTION BY EUKARYOTIC CELLS

[75] Inventors: Robert E. Rhoads; Arrico De Benedetti, both of Shreveport, La.

[73] Assignee: The University of Kentucky Research Foundation, Lexington, Ky.

[21] Appl. No.: 184,632

[22] Filed: Jan. 19, 1994

Related U.S. Application Data

[63] Continuation-in-part of Ser. No. 956,937, Oct. 5, 1992, abandoned, which is a continuation of Ser. No. 580,040, Sep. 10, 1990, abandoned.

[51] Int. Cl.$^6$ .............................. C12P 21/06; C12N 5/00; C12N 15/63
[52] U.S. Cl. ..................... 435/69.1; 435/320.1; 435/325; 435/367; 435/358; 435/359; 435/360; 435/366; 435/372.3; 435/372; 435/362
[58] Field of Search ............................... 435/69.1, 172.3, 435/240.1, 240.2, 320.1; 536/23.1

[56] References Cited

PUBLICATIONS

DeBenedetti et al., "Mammalian Expression Vectors for the in vivo study of eIF-4E", Abstr. Meeting on Translational Control, Cold Spring Harbor Laboratory, Cold Spring Harbor, NY, Sep. 1989.

DeBenedetti et al., "Over-Expression of eIF-4E, From an Episomal Vector in HeLa Cells results in Abnormal Growth and Ultimately Cell Death," Abstr. 2314, p. A2093, FASEB J. (1990).

Lazaris–Karatzas et al., "Malignant Transformation by a Eukaryotic Initiation Factor Subunit that Binds to mRNA 5" Cap", Nature, 345,544, (1990).

M. Kozak, "Selection of Translational Start Sites in Eukaryotic mRNAs," Current Communications in Molecular Biology, Cold Spring Harbor Laboratory, pp. 35–41, 1986.

De Benedetti, A. and R.E. Rhoads, "Overexpression of eukaryotic protein synthesis initiation factor 4E in HeLa cells results in aberrant growth and morphology," Proceedings of the National Academy of Science, vol. 87, pp. 8212–8216, Nov. 1990.

Joshi–Barve et al., "Alteration of the Major Phosphorylation Site of Eukaryotic Protein Synthesis Initiation Factor 4E Prevents its Association with the 48 S Initiation Complex," The Journal of Biological Chemistry, vol. 265, No. 5, pp. 2979–2983, (1990).

Hiremath et al., "In Vitro Synthesis, Phosphorylation, and Localization on 48S Initiation Complexes of Human Protein Synthesis Initiation Factor 4E," The Journal of Biological Chemistry, vol. 264, No. 2, pp. 1132–1138, (1990).

Rhoads, Robert E., "Cap recognition and the entry of mRNA into the protein synthesis initiation cycle," TIBS 13, Feb. 1988, pp. 52–56.

Fagan et al., "Translational Control of Ornithine Aminotransferase, Modulation by Initiation Factor eIF–4E," The Journal of Biological Chemistry, vol. 266, No. 25, pp. 16518–16523, (1991).

Koromilas et al., "mRNAs containing extensive secondary structure in their 5' non–coding region translate efficiently in cells overexpressing initiation factor eIF–4E," The EM80 Journal, vol. 11, No. 11, pp. 4153–4158, (1992).

Rychlik et al., "Amino acid sequence of the mRNA cap–binding protein from human tissues," Proceedings of the National Academy of Science, vol. S4, pp. 945–949, Feb. 1987.

De Benedetti, A. and R.E. Rhoads, "A novel BK virus–based episomal vector for expression of foreign genes in mammalian cells," Nucleic Acids Research, vol. 19, No. 8, pp. 1925–1931, 1991.

Shatzman, A.R. and M. Rosenberg, "[69]Expression, Identification, and Characterization of Recombinant Gene Products in *Escherichia coli*," Methods in Enzymology, vol. 152, Academic Press, Inc., 1987, pp. 661–673.

Sambrook et al., Molecular Cloning: A Laboratory Manual, 1989, pp. 16.3–16.72.

Sarkar et al., Biochimica et Biophysica Acta, 1984, vol. 783: pp. 122–129.

*Primary Examiner*—Mindy Fleisher
*Assistant Examiner*—Terry A. McKelvey
*Attorney, Agent, or Firm*—Lowe, Price, LeBlanc & Becker

[57] ABSTRACT

A hybrid vector carrying a first and second DNA segments operationally linked thereto, the first DNA segment encoding a protein capable of cross-linking to the cap structure of mRNA and mediating ribosome-binding, and the second DNA segment encoding a polypeptide or protein, the vector being capable of replication, transcription and translation to express the factor and the polypeptide or protein upon transformation of a eukaryotic host, and the polypeptide or protein being expressed at a level higher than the level of expression thereof in the absence of the first DNA segment. A eukaryotic host is transformed with this hybrid vector. Also disclosed is a method of increasing the synthesis of a polypeptide or protein in a eukaryotic host cell.

15 Claims, 20 Drawing Sheets

FIGURE 13

```
CGATCAGATCGATCTAAG
          -1
                    M   A   T   V   E   P   T   T   P   N   P   P   T   T   E   E   E   K   T   E   S   N
                    ATG GCG ACT GTC GAA CCG ACC ACC CCT AAT CCC CCG ACT ACA GAA GAG GAG AAA ACG GAA TCT AAT
                    1                   5                   10                  15                  20              25

Q   E   V   A   N   P   E   H   K   T   L   Q   N   R   W   A   L   F   F   K   N   D   K   S   T
CAG GAG GTT GCT AAC CCA GAA CAC AAA ATT CTA CAG AAC AGA TGG GCA CTC TTT TTT AAA AAT GAT AAA AGC ACT
        30                  35                  40                  45                  50                  55
90                                                      120

W   Q   A   N   L   R   L   I   S   K   F   D   T   V   E   D   F   W   A   L   Y   N   H   I   Q   N   L
TGG CAA GCA AAC CTG CGG CTG ATC TCC AAG TTT GAT ACT GTT GAA GAC TTT TGG GCT CTG TAC AAC CAT ATC CAG AAT TTA
        60                  65                  70                  75                  80                  85
180                                                     210                                                 240

M   P   G   C   D   Y   S   L   F   K   D   G   I   E   P   M   W   E   D   E   K   N   R   G   G   R   W   L   I
ATG CCT GGC TGT GAC TAC TCA CTT TTT AAG GAT GGT ATT GAG CCT ATG TGG GAA GAT GAG AAA AAC CGG GGA GGA CGA TGG CTA ATT
        90                  95                  100                 105                 110                 115
270                         300                                                         330

T   L   N   K   Q   R   R   S   D   L   D   R   F   W   L   E   T   L   C   W   T   T   E   S   E   D   Y
ACA TTG AAC AAA CAG CAG AGA CGA AGT GAC CTC GAT CGC TTT TGG CTA GAG ACA CTT TGC TGG ACT ACT GAG TCT GAA GAA TGT GAT GAC TAC
        120                 125                 130                 135                 140                 145
360                             390                                                         420

S   D   D   V   C   G   A   V   V   N   V   R   A   K   G   D   K   I   W   I   T   E   A   C   H   S   Q   Y   I   V   R   E   A
AGT GAT GAT GTA TGT GGC GCT GTT GTT AAT GTT AGA GCT AGG GGT GAT AAG AAA ATA TGG ATA GCA ACT GAG GAA TGT CAC TCC CAG TAT ATT GTG AGA GAA GCT
        150                 155                 160                 165                 170                 175
450                                                     480                             510

V   T   H   I   G   R   R   V   Y   K   N   R   E   F   V   V   H   A   D   T   A   T
GTT ACA CAT ATA GGG AGG GTA TAC AAG GAA TTT GTT GTT TAA GAAGACACCTTCTGAGTATTCTCATAGGAGACTGCGTCAAGCAATGAGACTTGGGAGCTGAACCA
        180                 185                 190                 195                                                 660                                                         720
540                                                                                                 570                                 690

K   S   G   T   S   T   K   N   R
AAG AGC GGC TCC ACC ACT AAA AAT AGG
                                                                                                                                                            840

AAGCCTCTCTTCAAAAAGCAGAGTGGACTGCATTGATTTGATTTCCATCTGAGTATTCTTACTCAGAGTATAAGAGAAGTCTCATTCGCCTTGTCTTGTCGTGTTCATTTTTTT
                                                                                                 750                                                     780                                                                                                 810
TTTTTTTTGGCTAGAGTTTCCACTATCCAAATCCAGAATTACAGTACACATCCCAGAATCCATAAATGTGTTCCTGGCCCACTCTGTAATAGTTCAGTAGAATTCATTAATTACAT
                                                                                                                 870                                                                                                     900                                                                                                         930                                                                                                                                                                         960
ACAGATTTACCTACCACAATAGTCTAGAAAACAACTTGGCATTTCTATACTTTACAGGAAAAAAAATTCTGTTGTTCCATTTTATGCAGAAGCATATTTTGCTGGTTTGAAAGATTATG
                                                                                                                         990                                                                                                 1020                                                                                                         1050                                                                                                                                                                         1080
ATGCATACAGTTTTCTAGCAATTTCTTTTGTTTTACAGCATTGTCTTTGCTGTGACATTGGTTTTAATTTATTGTTCCCTACTTGATAATATTAGTGAT
                                                                                                                         1110                                                                                                 1140                                                                                                         1170                                                                                                                                                                         1200
TCTGATTTCAGTTTTTTTGTTTCATTGTTTTTTTGTAAATTTTTTGTGCTTAAATTTTTGTGAAGGATCCAGGAATAACATTGGTGAAGGTGCACCAAAGGTGAACACAAAGGTGCATTC
                                                                                                                                 1230                                                                                                 1260                                                                                                             1290                                                                                                                                                                             1320
TTTGGTAATTTTTTTGTTTTTGTAACTACAAAGCTTTGCTACAAATTTATGCATTTCATTCAAATCAGTGATTTCTTTAAACACTTTGTATTTTAACACTTTGTGATTATTTGCTTTGGTTAAAAATGCCTCAAGTAG
                                                                                                                                                 1350                                                                                                                     1380                                                                                                                         1410                                                                                                                                                                                     1440
GTAACATCATAATTACATTCCTAACTAGAATTAGTAGTCTGTTTTGTATCTTTAATGCTGTATTTTAACACTTTGTATCTTGTATTTTAACACTGTAATAAATGTGTACAGTGACAATGAATTGTCCTTTTATTCTCCATCTTTATAGAAGAATTT
                                                                                                                                                         1470                                                                                                                             1500                                                                                                                                 1530                                                                                                                                                                                     1560
AAAAGCAGTCCATTCATATTAAGACAGTGTACAAAACTGTAATAAATGTGTACAGTGACAATGAATTGTCCTTTTATTCTCCATCTTTATAGAAGAATTT
                                                                                                                                                                 1590                                                                                                                                         1620                                                                                                                                                 1650                                                                                                                                                                                     1680
GTACTTCTTATTGCAGGCAAGTCTCTATATTATGTCCTTTGTGGTGTCTTCCATGTGAACAGCATAAGTTTGGAGCACTAGTTTGATTTGATTTATGTTTATTACAATTTTAATAAATT
                                                                                                                                                                 1710                                                                                                                                         1740                                                                                                                                                 1770                                                                                                                                                                                     1800
GAATAGTAGTATCATATATATGAAAAAAAAAAAAAAAAAAAAAAAAAAA
                                                                                                                                                                 1860                                                                                                                                         1880
```

HYBRID VECTOR AND METHOD RESULTING IN PROTEIN OVERPRODUCTION BY EUKARYOTIC CELLS

This application is a continuation-in-part application of Ser. No. 07/956,937, filed Oct. 5, 1992, now abandoned, which is a continuation of 07/580,040, filed Sep. 10, 1990, now abandoned.

TECHNICAL FIELD

This invention relates to a hybrid vector encoding a polypeptide with the mRNA-binding and ribosome-binding characteristics of eukaryotic protein synthesis initiation factor 4E (eIF-4E) and a second DNA segment encoding a protein, the first and second DNA segments being operationally linked to the vector and the vector being capable of replication, translation and expression of the polypeptide factor and the protein in a eukaryotic host upon transformation thereof, and the protein being expressed at levels higher than the level of expression thereof in the absence of the first DNA segment. The present invention provides for the overexpression of any protein or polypeptide whose DNA is operatively linked to the hybrid vector.

In addition, this invention also relates to a eukaryotic host transformed with the hybrid vector of the invention and to a method of increasing the synthesis of a polypeptide in a eukaryotic cell that comprises transforming a eukaryotic host cell capable of expressing a polypeptide at a specified level with a hybrid vector carrying DNA sequence encoding the MRNA and ribosome binding characteristics of EIF-4E, culturing the transformed cells in an expression medium and separating the polypeptide from the cells and the remaining medium. The present invention finds its utility in the area of protein production since it significantly increases the yield of a protein product.

BACKGROUND

Protein synthesis represents a major commitment of cellular energy and plays a fundamental role in nearly every aspect of metabolism. It also constitutes a critical step in the control of gene expression. The synthesis of each protein ultimately depends on the relative abundance of its MRNA and its intrinsic translatability, i.e. the capacity of that particular MRNA to interact with components of the translation machinery and be selected for translation. Cellular mRNAs vary over a 100-fold range in their translation efficiency. Additionally, their translation rates depend on the particular growth conditions of the cell. A theoretical treatment by Lodish, subsequently confirmed experimentally, postulates that the spectrum of translated mRNAs varies with the overall rate of protein synthesis. "Weak" mRNAs are outcompeted (i.e. are not translated) by "strong" mRNAs when the rate of translational initiation is reduced. In practice, "weak" mRNAs are not translated when the cell is quiescent; all mRNAs "weak and strong" are translated when the cell is active and capable of proliferation. These correlations should have placed protein synthesis at a pivotal position in pathways of growth control and cell differentiation. Instead, most scientific attention was focused on events occurring at the cell membrane, and then on how signals from the environment are transmitted to the cell nucleus and lead to the expression of previously inactive genes. Yet, it is significant that a surprising number of "weak" mRNAs are those encoding for many protooncogenes, e.g., c-myc, pp60-src, lck, mos, c-fos; growth factors, e.g. TGFβ, FGF, IL-1β, Insulin-like GF; growth-related genes, e.g., ornithine decarboxylase, ornithine aminotransferase, and the ribosomal proteins. All of the transcripts mentioned in these groups share the property of being cell-cycle regulated, and their protein products affect cell cycle progression.

Nevertheless, the hypothesis that a link must exist between the rate of protein synthesis and some regulatory function of cell growth has never been formulated. It is only because of very recent, and accidental findings, that these concepts are now emerging.

Because of the central role that protein synthesis has occupied throughout evolution, it is not surprising that translation rates are tightly regulated by some of the most sophisticated mechanisms known. In mammals most of the regulatory mechanisms thus far discovered operate at the step of translation initiation, rather than elongation or termination. The initiation process is envisions as comprising three steps: 1) formation of the 43S complex containing the initiation factors eIF-2, eIF-3, Met-tRNA and GTP, bound to a 40S ribosomal subunit; 2) formation of the 48S complex containing mRNA, which is mediated by the eIF-4 group of factors; 3) formation of the complete 80S complex upon joining of the 60S subunit.

In most circumstances, the regulation that takes place at the second step is rate limiting and specific, because one particular mRNA must be selected and recruited to the ribosomes. As mentioned above, this step is mediated by the eIF-4 group of factors, of which, eIF-4E is by far the least abundant and most likely the rate-limiting. The present inventors have show this experimentally with the application of antisense RNA technology since protein synthesis rates were directly proportional to the level of eIF-4E.

The initiation of translation in eukaryotes can be regulated at the level of 43S complex formation (binding of met-tRNA$_i$ to the 40S ribosomal subunit) and at the level of 48S complex formation (binding of mRNA to the 43S complex). The former occurs during virus infection, following interferon treatment, and in other severe and stressful circumstances. Under more normal cellular conditions, the formation of the 48S complex is rate limiting, and regulation by mitogens, growth factors, serum or during mitosis appears to occur at this step. mRNA binding to 43S complexes is catalyzed by the eIF-4 group factors, which collectively recognize the 7-methylguanosine-containing cap, melt mRNA secondary structure beginning from the 5' end, and facilitate the scanning of the mRNA sequence for the initiation codon by the 40S subunit.

Prior to the present invention, it was not completely understood how mRNA recruitment into 48S initiation complexes is regulated. A factor which is likely to be involved is eIF-4E, a 25-kDa polypeptide which binds to the cap (presumably the first step in mRNA recruitment) and accompanies mRNA transfer to the 48S complex. Whether eIF-4E acts as a free polypeptide, in a complex with other polypeptides, or both, has not been established. eIF-4E is the least abundant of the initiation factors and is present at approximately one-tenth the molar concentration of mRNA and ribosomes.

eIF-4E is a phosphoprotein, the major site of in vivo phosphorylation being Ser-53. Phosphorylation of eIF-4E is correlated with elevated protein synthesis in reticulocytes treated with phorbol esters, fibroblasts treated with serum, B lymphocytes activated with phorbol esters and ionomycin or lipopolysaccharide and 3T3-L1 fibroblasts treated with insulin. Conversely, dephosphorylation of eIF-4E is correlated with the inhibition of protein synthesis in HeLa cells after heat shock or during mitosis. Furthermore, a variant of eIF-4E in which Ser-53 is replaced with Ala-53 (eIF-4E$^{Ala}$) cannot be phosphorylated at the major in vivo site and is not found on the 48S initiation complex, suggesting that eIF-4E cannot participate in the transfer of mRNA to the 48S complex unless it is phosphorylated.

It was shown that when eukaryotic cells were transformed with a vector expressing the eIF-4E polypeptide factor (wild type), deleterious effects take place in the cell. In some cases, the expression of the eIF-4E factor was shown to be lethal to the cells whereas analogous cells containing the eIF-4E$^{Ala}$ variant were not (De Benedetti, A, et al, "Mammalian Expression Vectors for the in vivo Study of eIF-4E", Abstr., p.218, Translational Control, Cold Spring Harbor Laboratory, New York (1989). In another study, De Benedetti et al. (DeBenetti, A. and Rhoads, R. E., "Overexpression of eIF-4E from an Episomal Vector in HeLa Cell Results in Abnormal Growth and Ultimately Cell Death", Abstract 2314, FASEB Journal 4, A2093 (1990)), showed that when the eIF-4E gene is expressed from an episomal system, the wild type overexpresses the factor and accelerates cell growth and division as well as the formation of multi-nucleated cells. This was not the case when cells were transformed with a vector carrying the eIF-4E variant lacking the major phosphorylation site (wild type: SER-53, variant: Ala-53).

Fagan et al., *Journ. of Biol. Chem.*, Vol 266, No. 25, Sep. 5, 1991, p. 16518-16523 disclose an analysis of eIF4E mRNA in each of two different strains of retinoblastomas and its influence on the amount of ornithine aminotransferase in each of the strains of retinoblastomas. This publication does not disclose a hybrid vector according to the present invention.

Koromilas et al., *EMBO Journal*, Vol 11, No. 11, pp. 4153–4158 (1992) disclose that eIF4E overexpression facilitates the translation of mRNAs with 5' untranslated region (UTR) extensive secondary structures. This publication does not disclose a hybrid vector according to the present invention.

Shatzman and Rosenberg in Methods of Enzymology, Vol. 152 (1987) disclose the Shine-Delgarno sequence of prokaryotic messenger RNA. The Shine-Delgarno sequence provides an alignment between the mRNA and the 18S rRNA. This is important in the context of the correct positioning for translation initiation, but does not increase the rate of ribosome-binding of a particular mRNA. In eukaryotes, "stored" untranslated mRNAs can, at anytime, be recruited for translation, a reaction mediated by eIF4E. Thus, the knowledge that the binding of eIF4E to the 40S ribosomal subunit (mediated by eIF4E) is the rate limiting step for translation initiation, under normal conditions which was discovered by the present inventors and is distinct from prokaryotic translation initiation functions.

DISCLOSURE OF THE INVENTION

This invention relates to a hybrid vector that comprises
a vector carrying a first and second DNA segments operationally linked thereto;
the first DNA segment encoding a protein capable of cross-linking to the cap-structure of MRNA-binding and capable of mediating ribosome-binding; and
the second DNA segment encoding a polypeptide or protein; the vector being capable of replication, transcription and translation to thereby express the factor and the polypeptide or protein upon transformation of a eukaryotic host, and the polypeptide or protein being expressed at a level higher than the level of expression thereof in the absence of the first DNA segment.

This invention also relates to a eukaryotic host transformed with the hybrid vector described above.

In addition to the above this invention also relates to a method of increasing the synthesis of a polypeptide or protein in a eukaryotic host cell, the method which comprises obtaining a hybrid vector carrying a DNA segment encoding a factor having the mRNA-binding and ribosome-binding characteristics of EIF-4E; the vector being capable of replication, transcription and translation to thereby express the factor in a eukaryotic host;

transforming a eukaryotic host cell capable of expressing a polypeptide or protein at a certain level with the hybrid vector described above;

culturing the transformed cells in an expression medium to allow for the factor and the polypeptide or protein to be expressed; and separating the polypeptide or protein from the cells and the remaining medium.

A more complete appreciation of the invention and many of the attendant advantages thereof will be readily perceived as the same becomes better understood by reference to the following detailed description when considered in connection with the accompanying figures.

STATEMENT OF DEPOSIT

The hybrid vector of the present invention has been deposited under the terms of the Budapest Treaty with the American Type Culture Collection, 12301 Parklawn Dr., Rockville, Md., 20852 USA under ATCC Accession No. 98045 corresponding to BK-4E and 98046 corresponding to RDB-WT deposited on Apr. 30, 1996.

BKV ORI: viral origin of replication;

T/t Ag: large and small tumor antigens;

DRE-LTRP: dioxin-responsive enhancer and the promoter and the long terminal repeat of MMTV;

AMP: ampicillin-resistance gene;

pBR ori: bacterial origin of replication;

SV40:SV40 early promoter;

neo: neomycin-resistance gene (aminoglycoside phosphotransferase).

Figure 2:
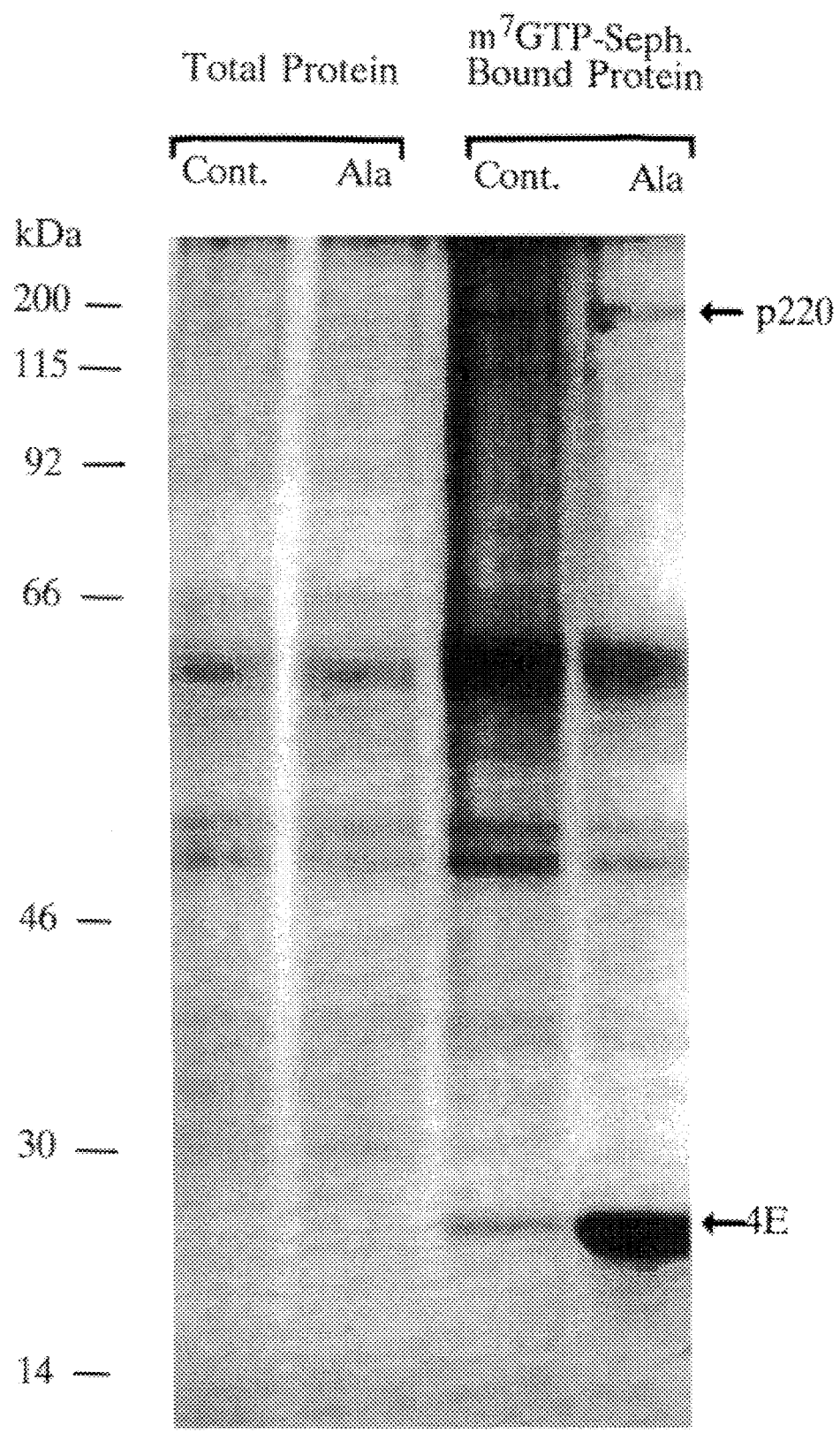

FIG. 2 is a picture of a sodium dodecyl sulfate polyacrylamide gel electrophoresis (PAGE). This figure shows a comparison of the amount of EIF-4E isolated from control HeLa and RDB-Ala-transformed cells. 20 ul of cell extract were used for visualization of total protein whereas 1 ml of cell extract was used for affinity purification of eIF-4E on m$^7$GTP-Sepharose. The arrows indicate the positions of the eIF-4E and the p220 component of eIF-4F. The results indicate that about 8 times more eIF-4E was expressed in transformed cells.

Figure 3A:
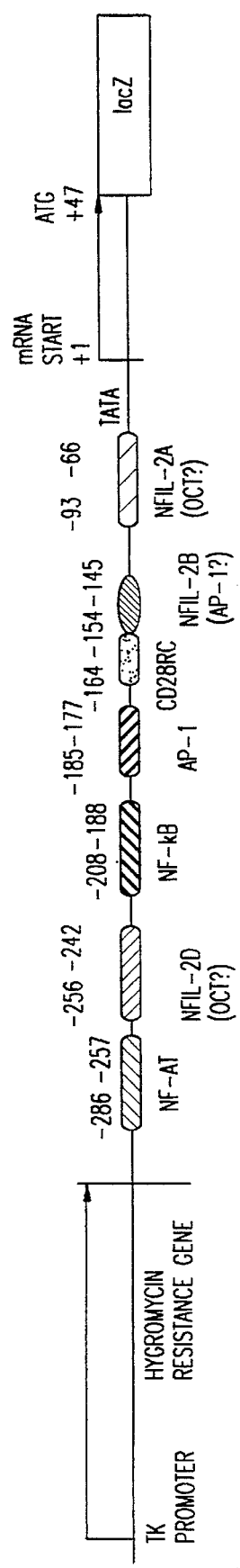

FIG. 3(A) shows a map of the human IL-2 enhancer-promoter/lacZ reporter construct used to transfect Th1 and Th2 clones. This includes the entire enhancer from −52 to –319. Sites that have been identified to bind proteins and are believed to contribute to transcriptional activation are noted.

Figure 3B:
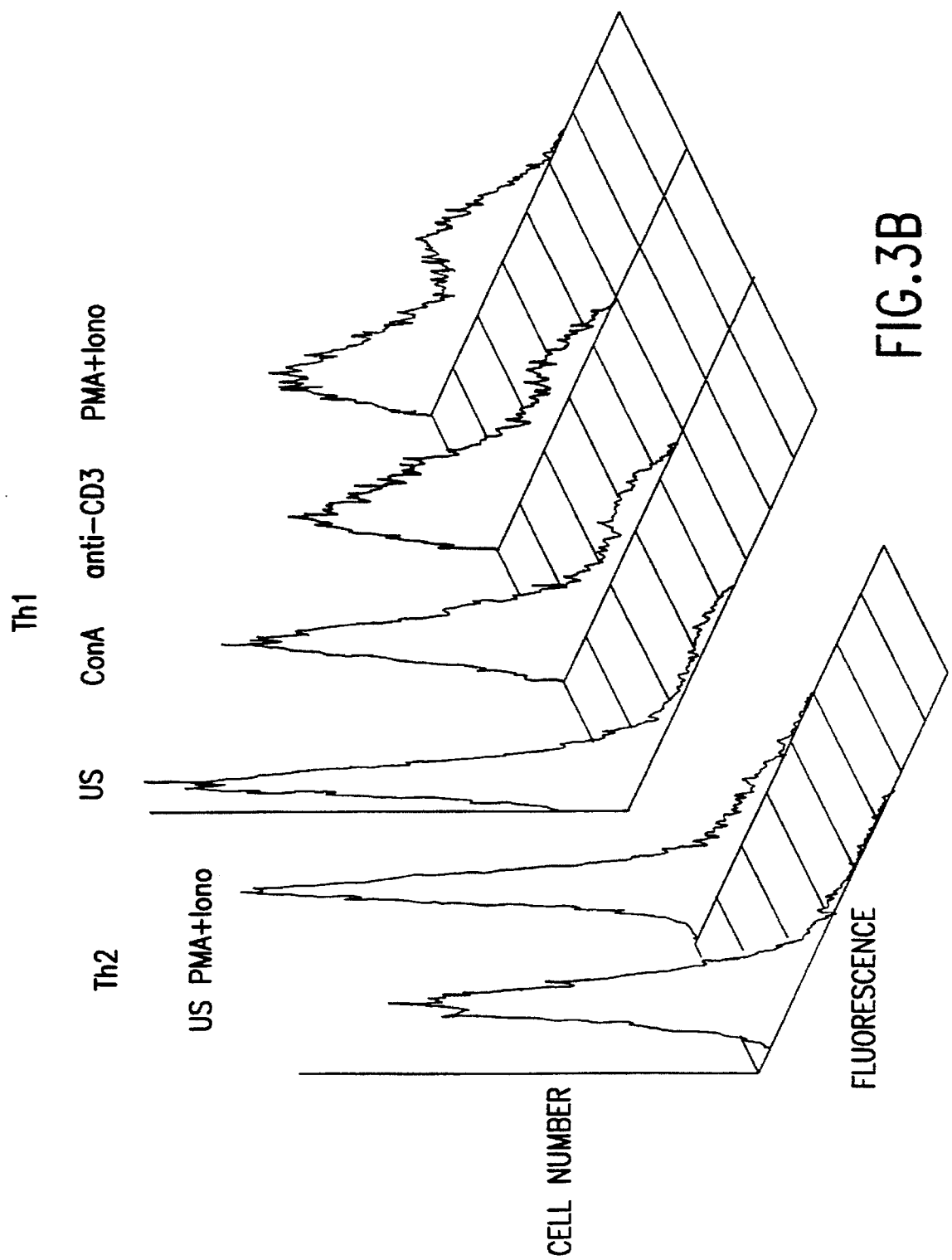

FIG. 3(B) shows analysis of lacZ expression directed by the human IL-2 enhancer in hIL-2/lacZ transfected murine Th1 and Th2 clones. The Th1 (S53) and the Th2 (S053) clones were stably transfected with the hIL-2/lacZ reporter construct (Fiering, S. et al. *Genes. Dev., Volume* 4, (1990) p. 1823) by the calcium phosphate method (Sambrook, J. et al. *Molecular Cloning: A Laboratory Manual* (Cold Spring Harbor Laboratory, New York, 1989)). Th1 and Th2 (hIL-2/lacZ) clones were activated using Con A (5 µg/ml), anti-CD3 (αCD3 plate bound) or PMA (10 ng/ml) and 2.25 µM ionomycin (PMA+Iono) as shown in the figure; unstimulated cells (US) that did not receive any treatment were used as a control.

Figure 4:
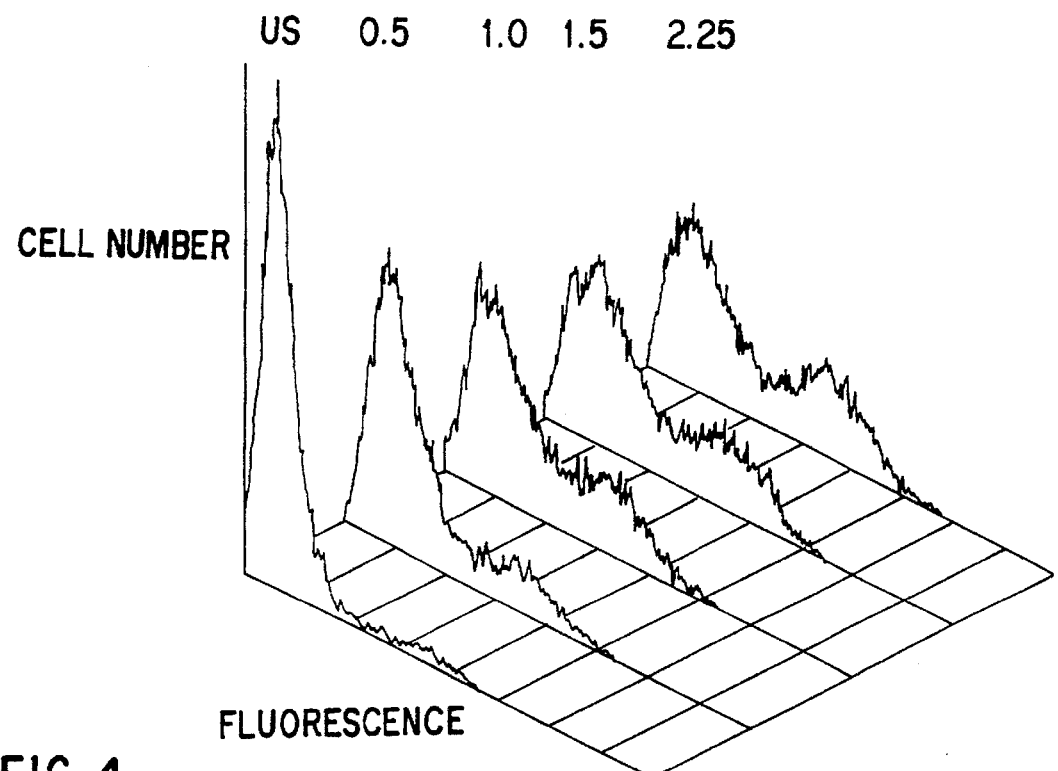

FIG. 4 shows analysis of the effect of ionomycin concentration on β-gal activity in a Th1 clone transfected with the hIL-2/lacZ construct. Cells were stimulated with 10 ng/ml PMA and varying concentrations of ionomycin (0.5 to 2.25 µM), harvested 18 hours after stimulation and β-gal expression analyzed as described in FIG. 1B. The percentage of β-gal+ cells at each concentration of ionomycin were: unstimulated control (US) –7%; 0.5 µM –23%; 1.0 µM –32%; 1.5 µM –37%; 2.25 µM –43%.

Figure 5:
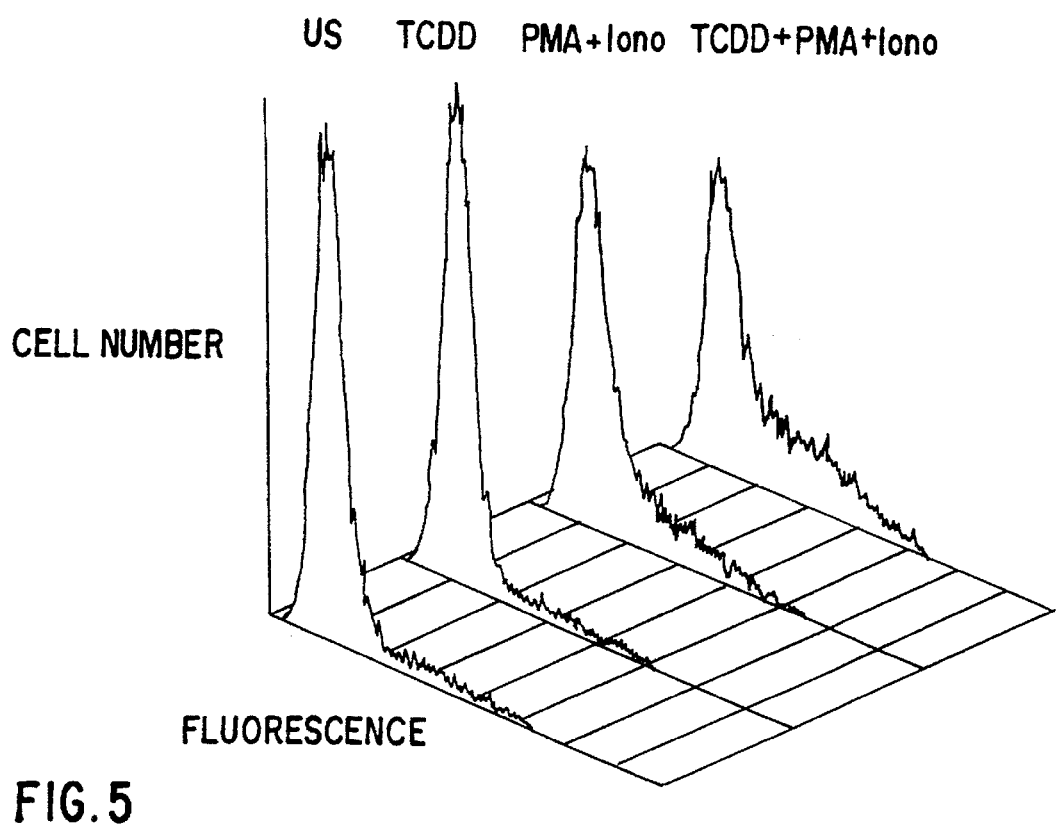

FIG. 5 shows analysis of the effect of eIF-4E on hIL-2/lacZ expression in Th2 cells. Th2 cells transfected with hIL-2/lacZ were further transfected with eIF-4E, selected and maintained using G418 (500 µg/ml). Experimental treatments were as follows: US—Unstimulated Control; TCDD (50 nM), to induce the eIF-4E construct; PMA+ Ionon—PMA (10 ng/ml) and ionomycin (2.25 µM); TCDD+ PMA+Iono—TCDD (50 nM), PMA (10 ng/ml) and ionomycin (2.25 µM). The percentage of cells which expressed β-gal were: UT –6%; TCDD –7%; PMA+Iono –21%; TCDD+PMA+Iono –29%.

Figure 6A:
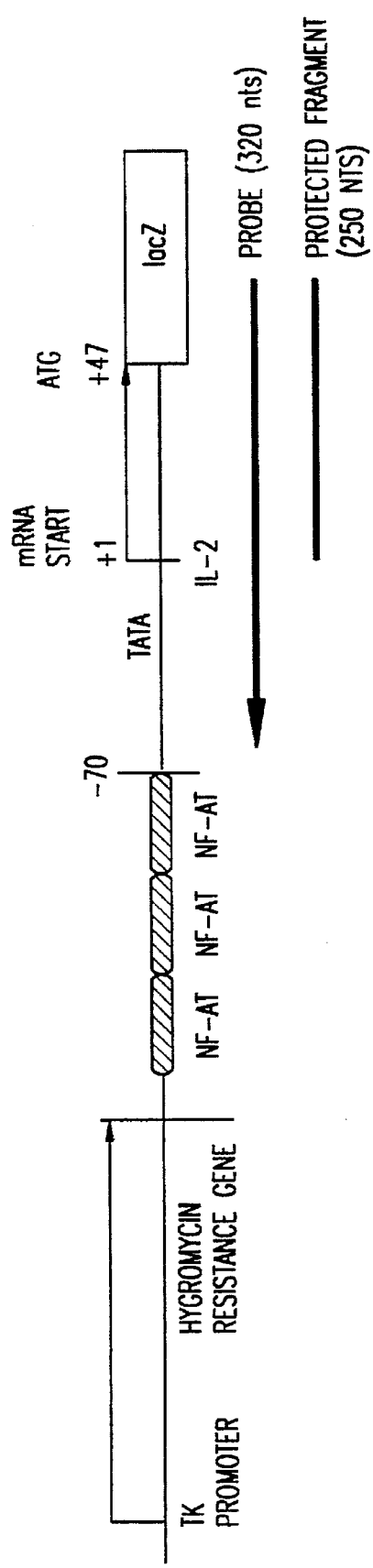

FIG. 6(A) shows a map of the NF-AT/lacZ reporter construct used to transfect Th1 and Th2 clones (Fiering, S. et al. *Genes. Dey., Volume* 4, (1990) p. 1823).

Figure 6B:
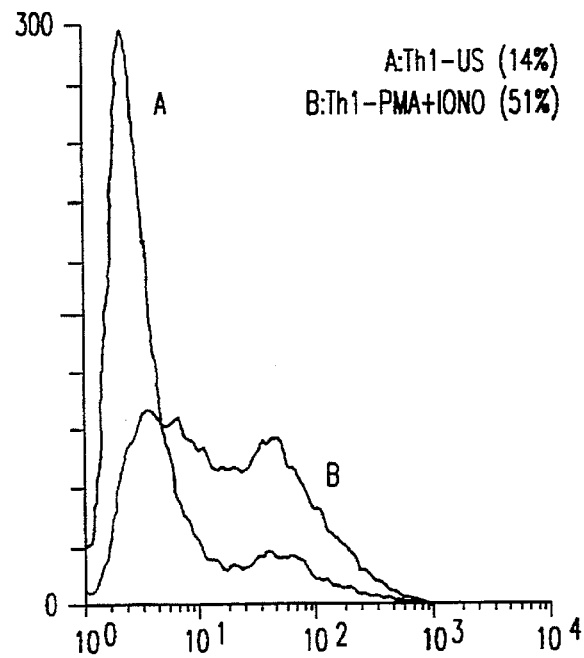
Figure 6C:
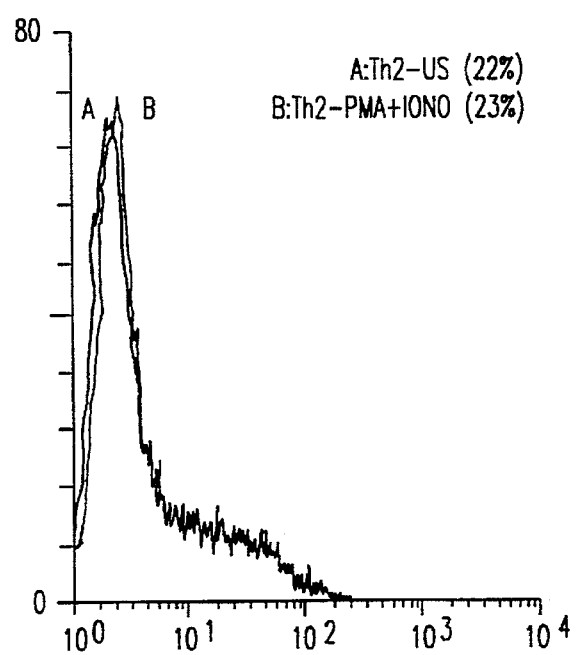
Figure 6D:
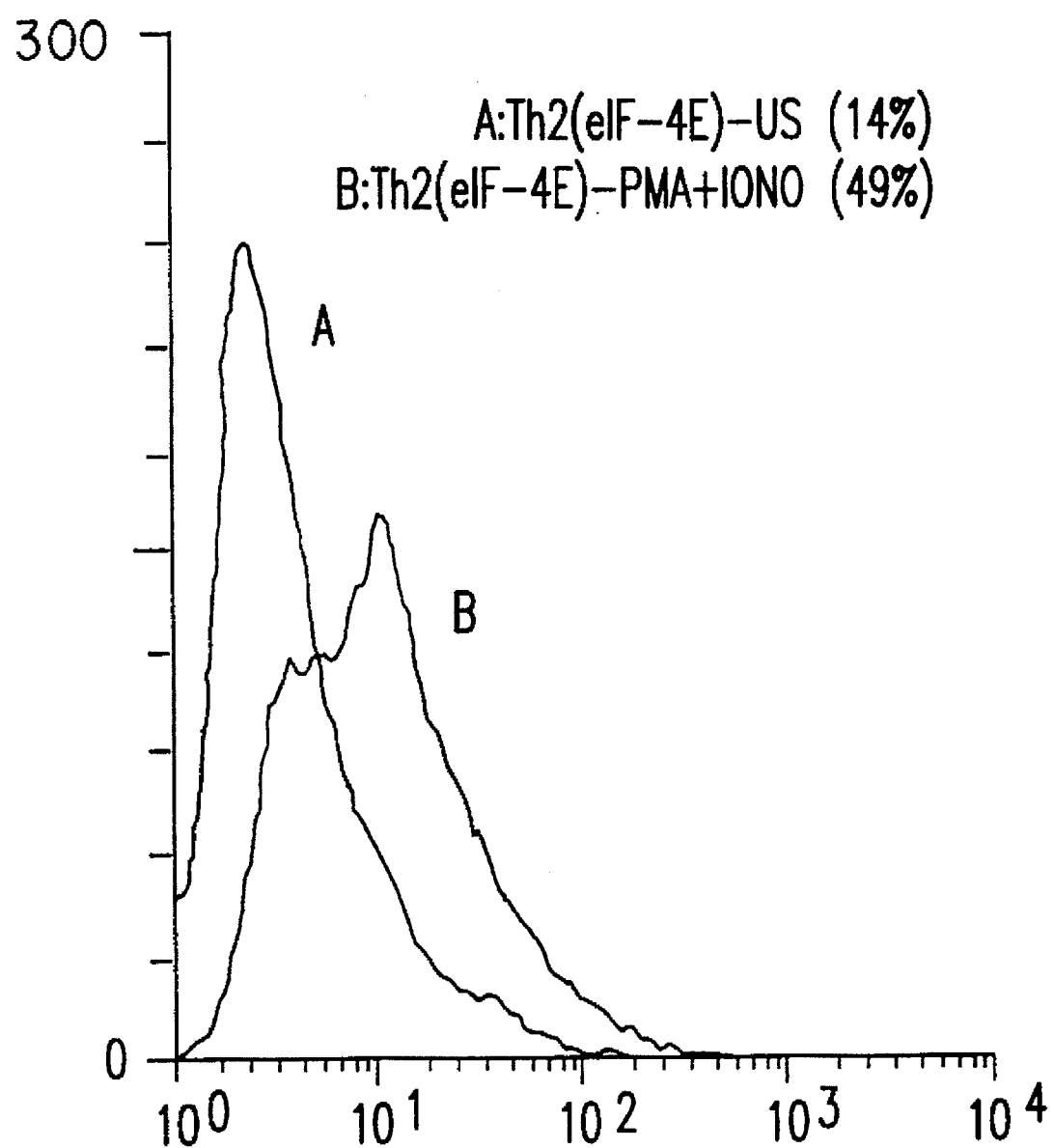

FIGS. 6(B)–6(D) show an analysis of the effect of eIF-4E on NF-AT/lacZ expression in Th2 cells. Different experimental treatments were as follows: US—Unstimulated control; (FIG. 6B) PMA+Iono—PMA (10 ng/ml) [FIG. 6C] and ionomycin (2.25 µM) (FIG. 6D). Cells were harvested at 18 hours and β-gal expression analyzed as described in FIG. 1, to monitor NFAT-dependent lacZ expression. The percentage of cells which expressed β-gal is indicated in parenthesis.

Figure 6E:
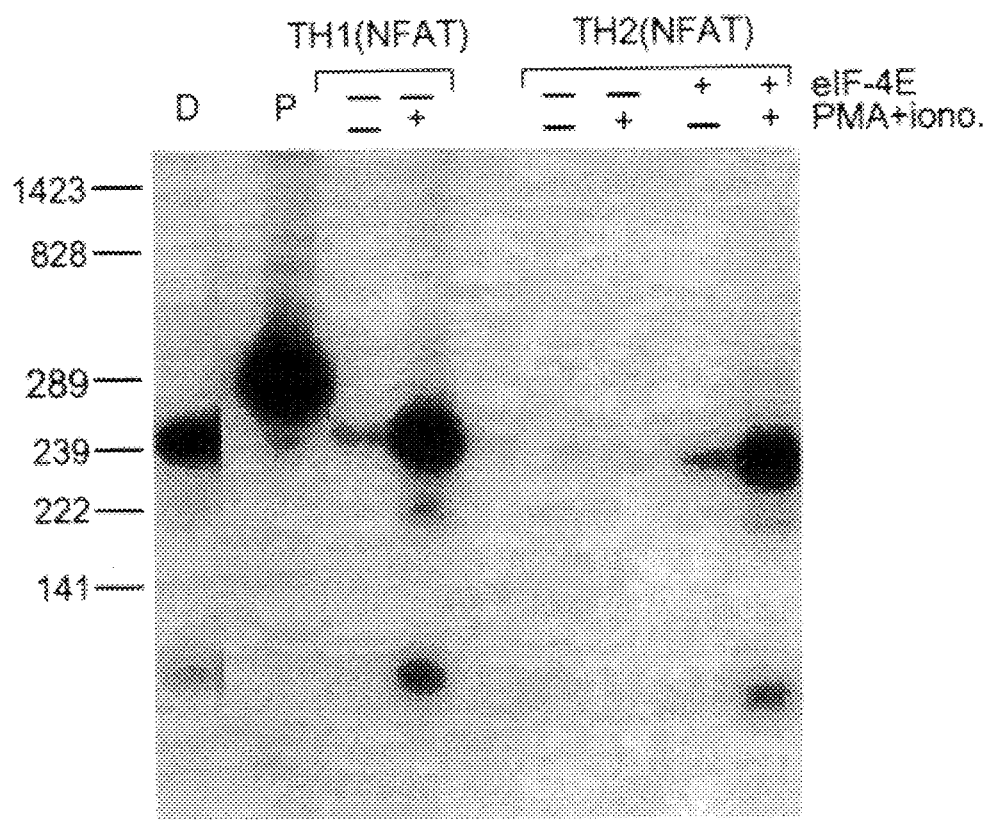
Figure 7A:
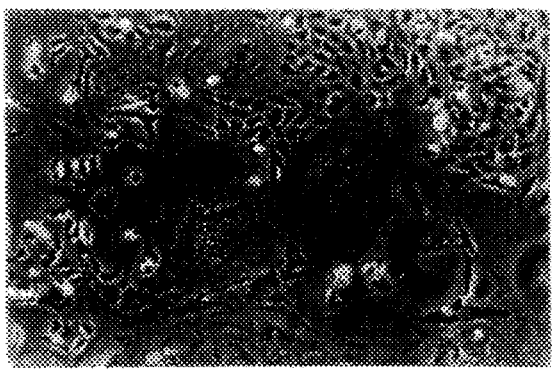
Figure 7B:
Figure 7C:
Figure 7D:

FIG. 6(E) shows determination of the chimeric IL-2/lacZ mRNA from the NF-AT/lacZ construct by the RNase protection assay. A 320 nt minus-sense $^3$H-labeled RNA was prepared form PstI-digested pSP65Gal (Fiering, S. et al. *Genes. Dev.,* Volume 4, (1990) p. 1823). The arrow shows a 250 nt-protected fragment, as expected from a properly initiated IL-2 transcriptional initiation start site.

FIGS. 7A–7D show the effect of eIF-4E overexpression in HeLa cells, a stably transformed HeLa cell line was obtained. These cells grow as a persistent mixture of two populations: one composed of rapidly dividing cells, the other represented by gigantic multinucleated cells which frequently fuse to form syncytia (top left frame).

Figure 8:
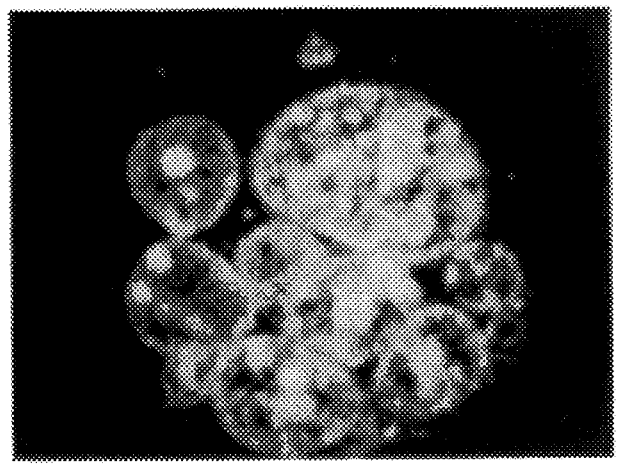

FIG. 8 shows the multinucleation phenomenon in greater details. Here a single cell, stained with propidium-iodide (chormatin-dye), is viewed by confocal microscopy. Addition of TCDD to the medium (to induce maximal levels of eIF-4E) results in a nearly complete conversion of HeLa-4E cells to the multinucleated phenotype.

Figure 9:
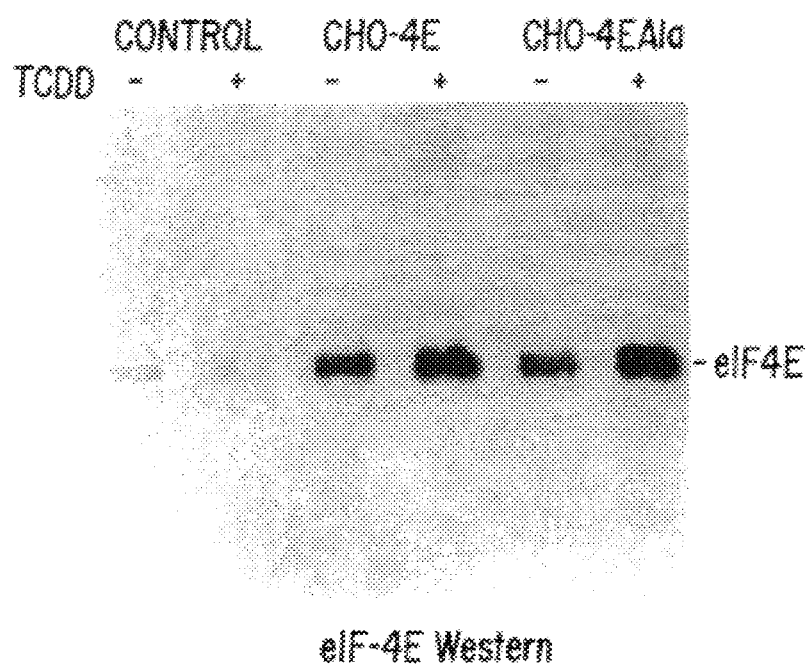

FIG. 9 shows the basal level of overexpressed eIF-4E was 3.5-fold, and 10-fold after TCDD-induction, for both CHO-4E and CHO-4EAla cells.

Figure 10:
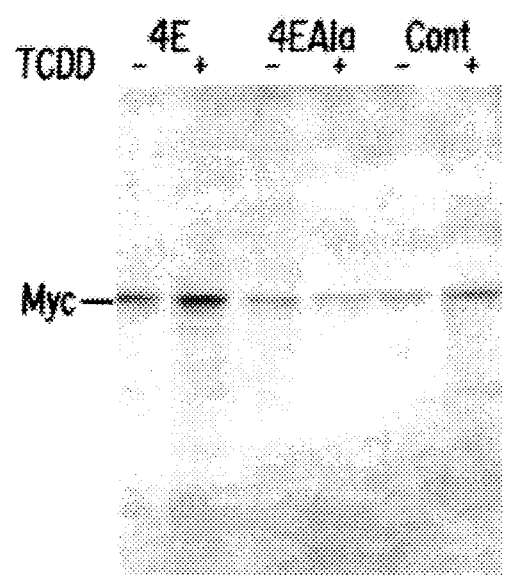

FIG. 10 shows overexpression of eIF-4E in CHO (CHO-4E) cells leads to a specific (4-fold) increase in c-myc expression.

Figure 11A:
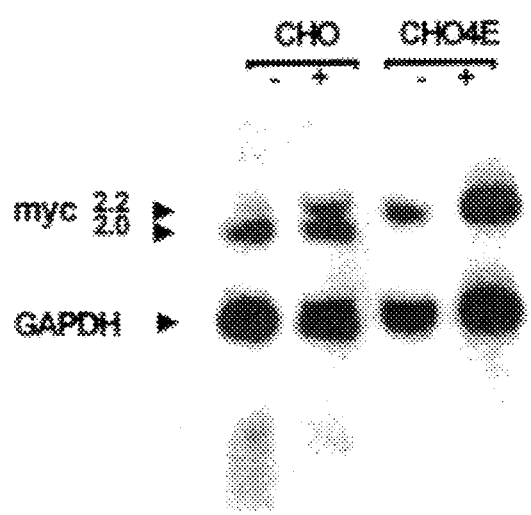
Figure 11B:
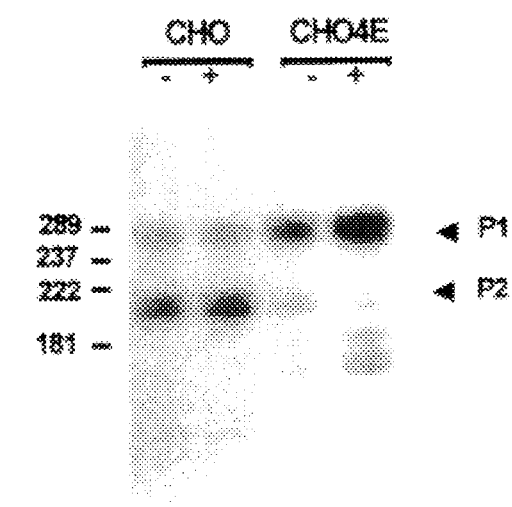
Figure 11C:
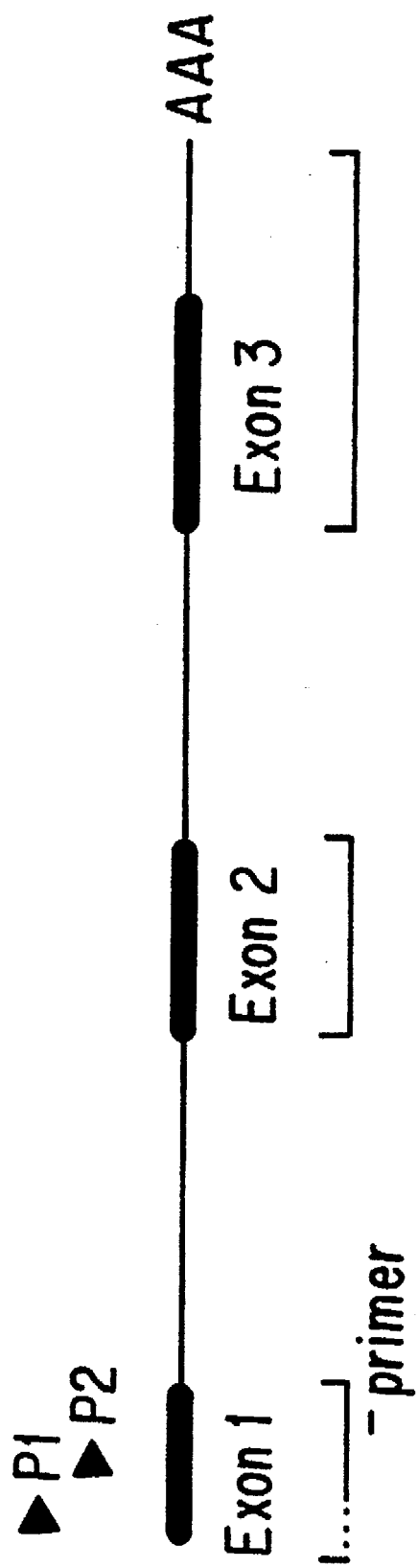

FIGS. 11A–11C show an unexpected finding of this work was a reversion in the level of P1 vs. P2-initiated c-myc transcripts in CHO-4E cells.

Figure 12:
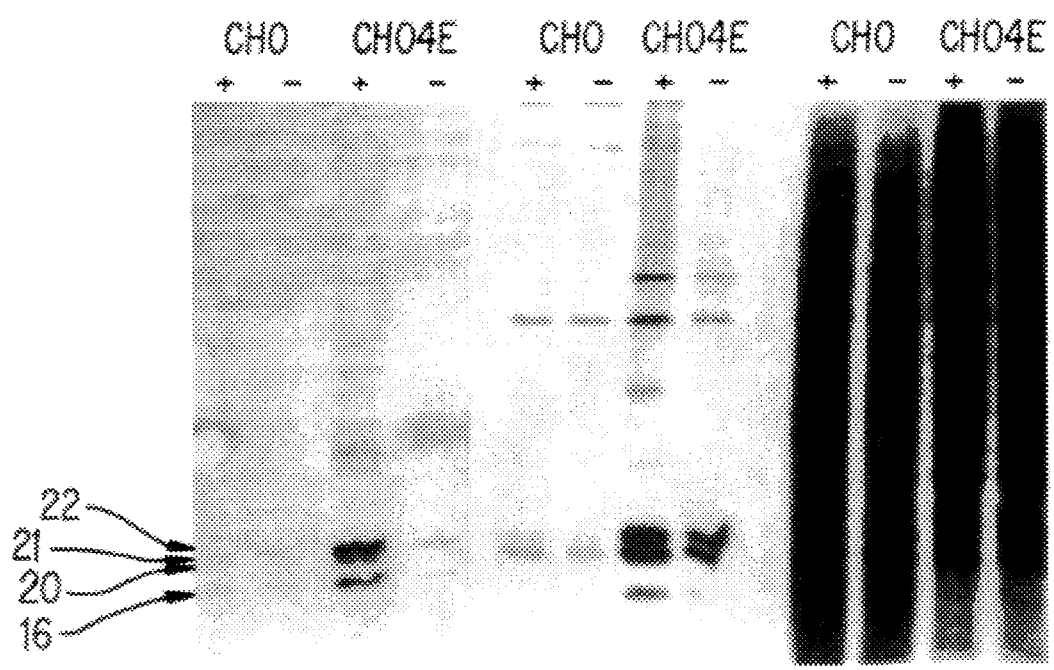

FIG. 12 shows immunoprecipitations and western-blot analyses of CHO vs. CHO-4E cells revealed a dramatic (>20-fold) increase in the expression of bFGF.

FIG. 13 shows the cDNA sequence (SEQ ID NO: 1) of eIF4E as reported in Rchylik et al., *Proc. Nat. Acad. Science,* Vol. 84 (1987) p. 945-949.

Figure 14A:
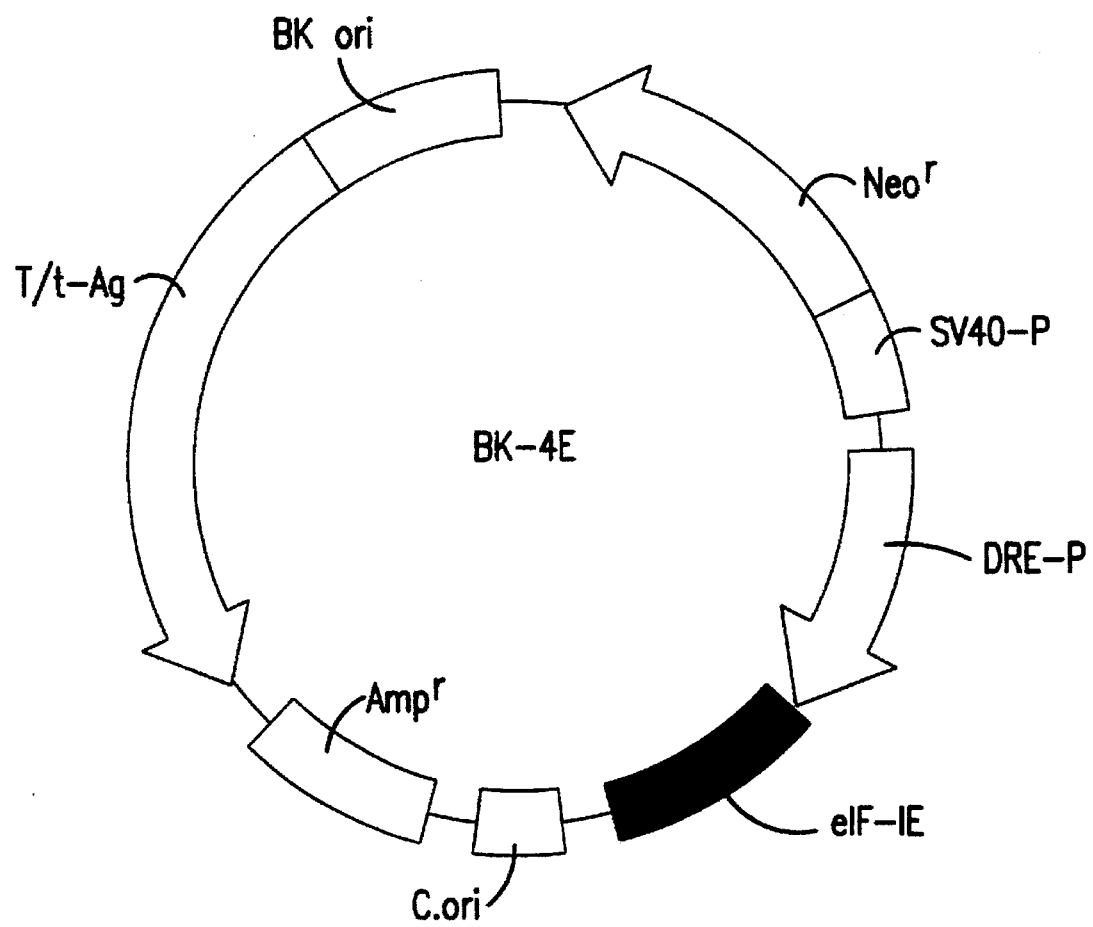
Figure 14B:
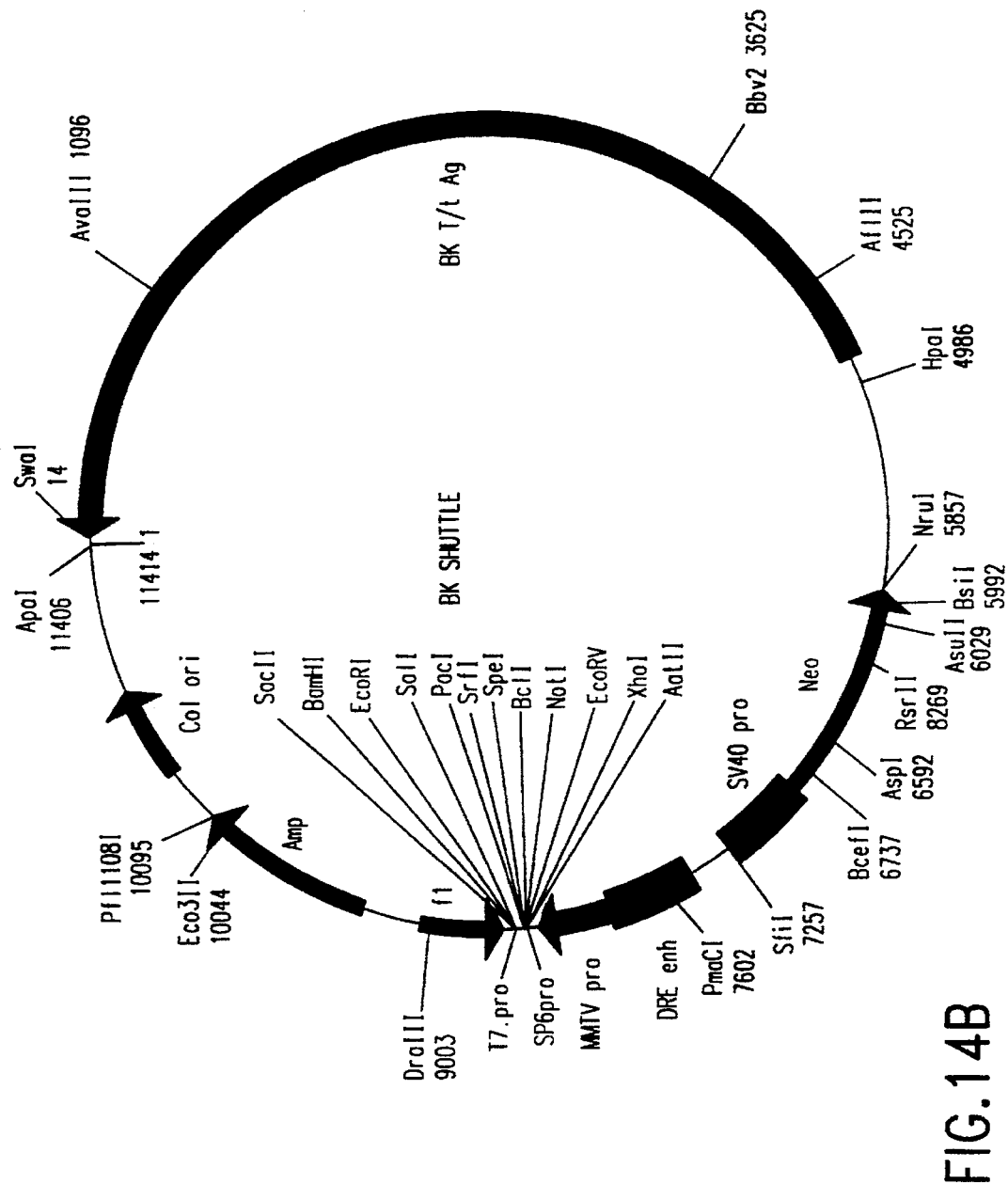

FIGS. 14(A)–14(B). FIG. 14(A) shows vector BK-4E and FIG. 14B shows modified vector RDB-WT.

Figure 15:
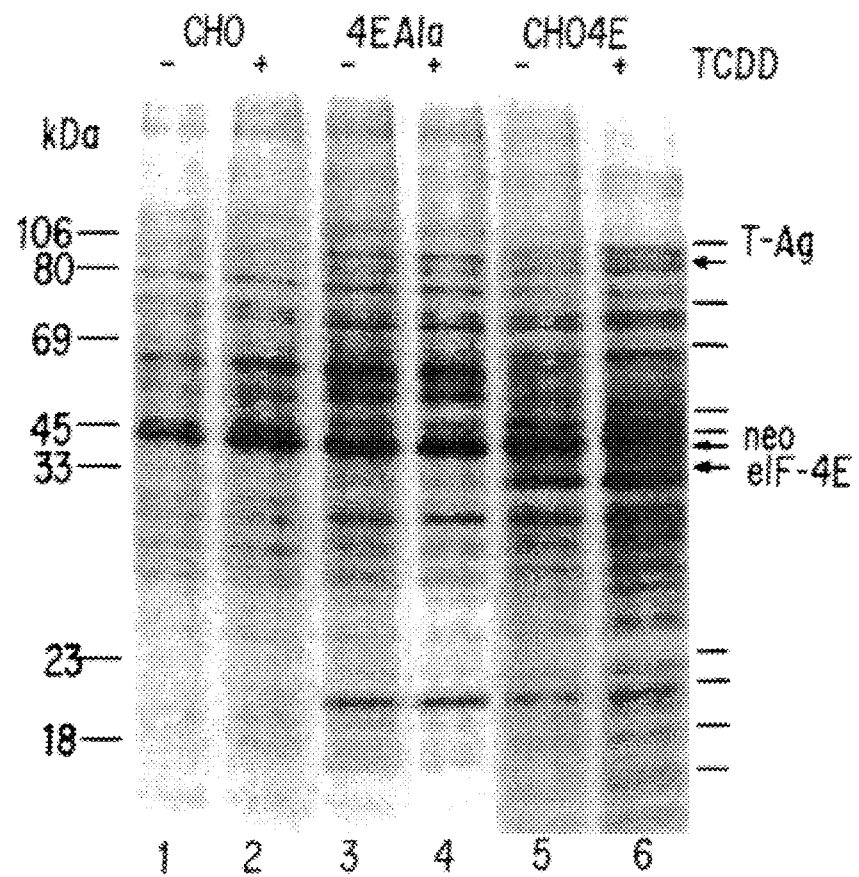

FIG. 15 shows overexpression of neomycin protein when part of the RDB vector.

Other objects, advantages and features of the present invention will become apparent to those skilled in the art from the following discussion.

DISCLOSURE OF THE INVENTION

This invention arose from the desire by the inventors to improve on known methods of polypeptide and protein synthesis conducted by cultivation of eukaryotic cells.

Up to the present time cells capable of producing a large amount of a desired protein were cultured in an expression medium and allowed to accumulate the desired protein. The protein was then separated from the rest of the medium and the cells. In many instances, however, the level of production of a desired protein is low or, in any case, it would be economically beneficial to obtain higher levels of production of a determined polypeptide or protein with the same materials and substantially the same period of time.

Accordingly, this invention provides a method of increasing the synthesis of a polypeptide or protein in a eukaryotic host cell that comprises obtaining a hybrid vector carrying a DNA segment encoding a protein capable of cross-linking to the cap structure of mRNA and mediating ribosome-binding; the vector being capable of replication, transcription and translation to thereby express the factor in host;

transforming a eukaryotic host cell capable of expressing a polypeptide or protein at a specified level with the hybrid vector described above;

culturing the transformed cells in an expression medium to allow for the factor and the polypeptide or protein to be expressed; and separating the polypeptide or protein from the cells and the remaining medium.

The eukaryotic protein synthesis initiation factor (eIF-4E) has been known for its importance in the mechanism of synthesis of protein of eukaryotes (Rhoads, R., *Trends Biochem. Sci.* 13, 52–56 (1988); Sonenberg, N., *Prog. Nucl. Acid Res. Mol. Biol.,* 35, 173–207)).

The cDNA encoding the factor has been sequenced in several species, e.g., human, yeast, and mouse (human: Rychlik, W., Domier, L. L., Gardner, P. R., Hellman, G. M. and Rhoads, R. E., *Proc. Natl. Acad. Sci.* (U.S.A.) 84, 945–949 (1987) (see FIG. 13); yeast: Altmann, M., Handschin, C., and Trachsel, H., *Mol. Cell. Biol.* 7, 988–1003 (1987); mouse: McCubbin, W. D., Edery, I., Altmann, M., Sonenberg, N. and Kay, C. M., *J. Biol. Chem.* 262, 17663–17671 (1988)).

The technology for the preparation of the hybrid vector carrying DNA segments is known in the art. Vectors suitable for use in the present invention are those that contain at least DNA sequences which enable the vector to replicate and transcribe itself and translate any products encoded in DNA segments operatively linked to it in reading frame, to thereby express any polypeptide or protein encoded in the DNA segments in a eukaryotic host. Such vectors are known in the art and need not be further described herein (Sambrook, J., Fritsch, F. F., and Maniatis, T., Molecular Cloning. A Laboratory Manual, Vol. 3, Chapter 16, second edition, Cold Spring Harbor Laboratory Press (1980)).

The hybrid vector may have operatively linked thereto a single DNA segment encoding one or more copies of the (EIF-4E) factor, and optionally a second DNA segment encoding a polypeptide or protein desired to be synthesized. The latter is also operatively linked to the vector so that the sequences in the vector and the DNA segments are in reading frame. Other DNA segments may also be added to the vector as is known in the art. Again, the technology suitable for attaining the formation of such hybrid vector is known in the art (Sambrook et al, supra). In one example of the present invention, the protein neomycin (neo) present on the RDB vector was overexpressed.

Alternatively, the second DNA segment encoding for a protein or polypeptide to be synthesized may be provided in a separate hybrid vector, in the form of an episome or incorporated into the genome of a eukaryotic cell. The technology for practicing this invention is also known in the art (Graham, F. L., and van der Eb, A. J., Virology 53,456–467 (1973) and incorporated herein by reference).

The technology suitable for transformation of a eukaryotic host cell with a hybrid vector is also known in the art and need not be further explained herein (Kingston, R. E., Kaufman, R. J. and Sharp, P. A., Mol. Cell. Biol. 4, 1979–1977 (1984) and incorporated herein by reference).

The conditions for transformation may be tailored in accordance with the specific vector and/or host utilized as is known in the art.

The cells are cultured in an expression medium so that the EIF-4E factor may be expressed in amounts sufficient to increase the synthesis of the protein or polypeptide. This step is conducted for a period of time effective to attain a level of protein or polypeptide production that is desired. Typically, the step is conducted for about 1 to 5 days, and preferably about 2–3 days. Suitable expression media are known in the art and need not be further described herein (Jones, P. B. C., Durrin, L. K., Galeazzi, D. R., and Whitlock, J. P., Proc. Natl. Acad. Sci. U.S.A. 83, 2802–2806 (1986) and incorporated herein by reference).

The separation of the thus produced polypeptide or protein from the rest of the expression medium and the cells is also conducted with technology known in the art (Sambrook et al., supra).

The method of the invention provides significantly increased levels of polypeptide or protein synthesized. Typically, the polypeptide or protein is obtained in an amount in excess of about 1.5 times the level of production in the absence of the eIF-4E factor, and in some instances at an even greater level. Protein overexpression is in a range of about 1 to about 20 times is normal cell expression.

Also provided herein is a hybrid vector that comprises
a vector carrying a first and second DNA segments operationally linked thereto;
the first DNA segment encoding a protein capable of cross-linking to the cap structure of mRNA and mediating ribosome-binding; and
the second DNA segment encoding a polypeptide or protein, the vector being capable of replication, transcription and translation to thereby express the factor and the polypeptide or protein upon transformation of a eukaryotic host, and the polypeptide or protein being expressed at a level higher than the level of expression thereof in the absence of the first DNA segment.

This vector typically comprises sequences that enable it to replicate and transcribe itself and other DNA segments attached thereto in a eukaryotic host as well as translating other products encoded by DNA segments, to thus express the polypeptide or protein encoded therein.

Further provided is a hybrid vector wherein the second DNA segment encodes a polypeptide or protein selected from the group consisting of chloramphenicol acetyl transferase, neomycin phosphotransferase, insulin, interferon, growth hormone, bFGF, oncogenes, tissue plasminogen activator, hepatitis B vaccine, endorphins, and interleukins.

In addition, the vector may also comprise DNA sequences which permit its replication and transcription as well as translation to express products in prokaryotic hosts. This characteristic may be utilized for the preparation of the hybrid vector prior to its utilization in the present method (Southern, P. J., and Berg, P., J. Molec. and App. Gen. 1, 327–341 (1982)).

The preparation of the DNA segments and the vector for cloning is also conducted in accordance with technology known in the art (Milanesi, G., Barbanti-Brodano, G., Negrini, M., Lee, D., Corallini, A., Caputo, A., Grossi, M. P. and Ricciardi, R. P., Mol. Cell. Biol. 4, 1551–1560 (1984)).

The DNA fragments are ligated as is known in the art (Sambrook et al (II), Molec. Cloning. A Lab Manual, Vol. 1, 2nd Ed., Cold Spring Harbor Lab. Press (1989)).

The hybrid vector may be kept under refrigeration or at lower temperatures by freezing in a sealed container. The hybrid vector may be withdrawn from the freezer and thawed prior to use as is known in the art. The hybrid vector may be amplified utilizing technology known in the art (Sambrook et al., (II), supra).

It is important that the mRNA-binding and ribosome-binding characteristics of the eIF-4E factor be present in the factor or fragment thereof. Thus, fragments thereof having a lesser number of amino acids are also suitable as are the DNA segments encoding them. Typically, fragments about 10 to 1000 amino acids long, and preferably 200 to 500 amino acids long, are suitable as long as they have the above characteristics preserved.

The polypeptide or protein to be synthesized is encoded by the second DNA segment may be any polypeptide or protein. Suitable are polypeptides or proteins about 10 to 1000 amino acids long, and preferably about 200 to 500 amino acids long. However, polypeptides and proteins of other sizes may also be utilized for cloning into a vector within the limits of size known in the art (Pestka, S., ed., Methods in Enzymology, Vols. 78–79, Interferons A and B, Academic Press, N.Y. (1981)).

Examples of polypeptides or proteins suitable for cloning of DNA segments encoding them into a vector as described herein are neomycin, BK virus T-antigen (necessary for vector replication), insulin, interferon, growth hormone, tissue plasminogen activator, hepatitis B vaccine, endorphins, interleukins, oncogenes, bFGF and the like.

In a particularly preferred embodiment of the hybrid vector, the polypeptide encoded in the first DNA segment encoding a protein which comprises the eIF-4F factor or a functional fragment thereof.

In another preferred embodiment the vector comprises eukaryotic viral sequences which permit its replication and transcription as well as the expression of encoded amino acid sequences in a eukaryotic host.

In still a most preferred embodiment of the hybrid vector, the first DNA segment comprises the eIF-4E cDNA.

The hybrid vector of the invention may carry multiple copies of the first as well as the second DNA segments. Typically, the number of copies of each DNA segment may be 1 to 2, but the number of copies of the vector inside the transformed cell could be as high as 10,000.

Also provided herein is a eukaryotic host transformed with the hybrid vector of the invention described above. Suitable eukaryotic hosts are mammalian cells such as HeLa cells, continuous rat embryo fibroblast (CREF) Cells, CHO cells, insect cells, plant cells such as tobacco protoplasts, yeast cells and the like. However, other eukaryotic cells may also be utilized.

Having now generally described this invention, the same will be better understood by reference to certain specific examples, which are included herein for purposes of illustration only and are not intended to be limiting of the invention or any embodiment thereof, unless so specified.

EXAMPLES

Example 1: Expression vectors.

Figure 1:
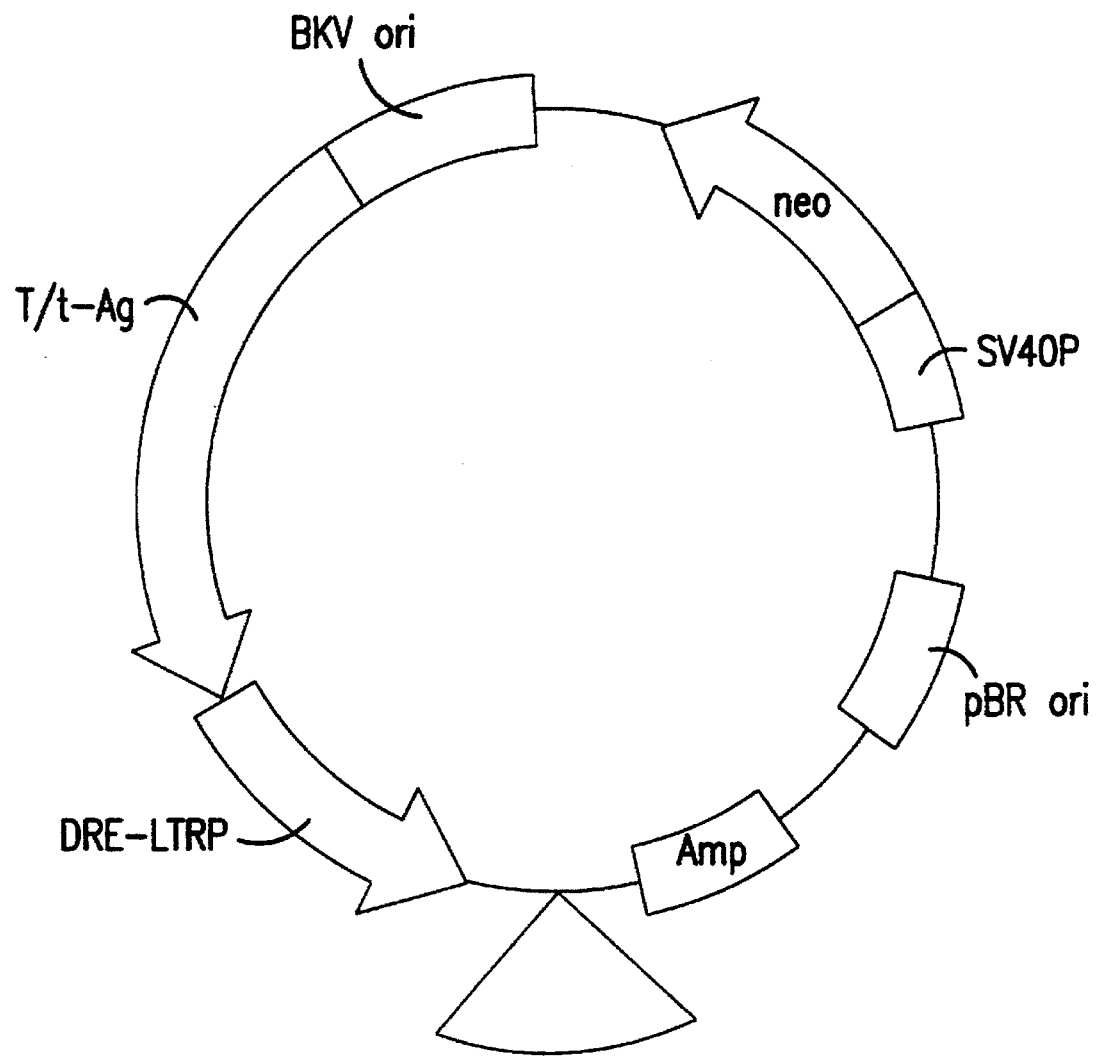
FIG. 1 provides an outline of the vectors RDB-Wt, RDB-Ala and RDB-CAT utilized in the examples. The arrows indicate the direction of transcription. The thick arc following the MMTV promoter indicates the genes inserted to form the various vectors. The abbreviations included in the boxes correspond to the following.

The RDB vector is a composite which includes most of the BK Papova virus (Seif, I. et al, Cell 18, 963–977 (1979)); sequences from pSV2-neo (Southern, P. G. and Berg, P., J. Molec. & Applied Gen. 1, 327–341 (1982)); and pGem7 (Promega Biotec, Madison, Wisc.) sequences for bacterial origin of replication and multiple cloning sites. The vector is shown in FIG. 1. RDB-0 is the vector with no insert in the multiple cloning site.

The cDNA encoding eIF-4E$^{Ser}$ is contained within the plasmid pTEEC (Hiremath, L. S., et al, J. Biol. Chem. 264, 1132–1138 (1985) incorporated herein by reference) whereas the cDNA for eIF-4E$^{Ala}$ is in the plasmid pTCALA (Joshi-Barve, S. et al, J. Biol. Chem 265, 2979–2983 (1990)). pTCEEC was cut with ClaI and Hind-III and the EIF-4E$^{Ser}$-encoding fragment inserted in the corresponding sites of the polylinker of pGEM7. PTCALA was cut with PvuII and BamHI. After the addition of a Hind-III linker to the blunt PvuII-cut end, the eIF-4E$^{Ala}$-encoding fragment was cloned in the corresponding sites of the polylinker of pGEM7. Finally, the 3'-terminal non-coding regions of the two inserts were rendered identical by removal of the sequence 1080–1269 (using the numbering system of 18) of the eIF-4E inserts, in the form of a NsiI fragment extending from position 1080 to the NdiI site of pGem7. The nucleotide sequence of cDNA corresponding to cap binding protein (eIF-4E) mRNA was reported in Proc. Nat. Acad. Science, Vol. 84 (1987) p. 945–949 and is set forth in FIG. 13, "SEQ ID NO:1".

The CAT gene was isolated by cutting plasmid pMcat4.1 (Jones, P. B. C., Durrin, L. K., Galeazzi, D. R., and Whitlock, J. P., Proc. Natl. Acad. Sci. (U.S.A.) 83, 2802–2806 (1986)) with Hind-III and BamHI and was inserted into the Pgem7 polylinker. In the case of all three pGEM7 constructions (eIF-4E$^{Ser}$, eIF-4E$^{ala}$ and CAT), the modified BK virus was cut with EcoRI and SalI and inserted between the EcoRI and XhoI sites of the polylinker.

Example 2: Cell transfection and selection.

HeLa cells (ATCC-CCL2) were obtained from the American Type Culture Collection and cultured in Dulbecco's modified Eagle's medium with 10% fetal bovine serum in 100×20 mm dishes. The cells were washed twice with medium minus serum before addition of a 2-ml suspension containing 20–30 µg plasmid DNA in Hepes-buffered saline and 0.08 M CaCl$_2$. After 20 minutes, 5 ml of complete medium were added for 5 hours. After recovery for 24 hours in fresh medium, the cells were plated in 75-cm$^2$ flasks. G418 selection at 0.2 mg/ml was begun the next day. The medium was changed daily for 4 days and thereafter once a week. The cells were grown as mass cultures.

Example 3: Microscopic observations and photographs.

Cells were viewed through a Nikon N4004 microscope at 20X with a green/amber filter. For photography, a Nikon 2020 camera was used with Kodak 400 T-max film.

Example 4: Isolation of eIF-4E.

eIF-4E from control HeLa cells and RDB-Ala transformed cells was isolated from cytoplasmic cell extracts on a m$^7$GTP-Sepharose column (Pharmacia P-L, Piscataway, N.J.) following the procedure of Webb et al. (Webb, N. R., Biochemistry 23, 177–181 (1984)). Approximately 3×10$^7$ cells (one confluent 225-cm$^2$ flask) were lysed in two volumes of 20 mM Hepes (pH 7.6), 20 mM KOAc, 0.1 mM EDTA, 0.2 mMATP, 0.2 mM GTP and 1% Triton X-100. The protein bound to the column was eluted with 1 ml of 0.1 M m7GTP and precipitated by the addition of 0.1 ml 100% trichloroacetic acid. After extensive washing with acetone, the portion pellet was dried and dissolved in sample buffer for NaDodSO$_4$/PAGE analysis (Laemmli, U.S., Nature 227, 680–685 (1979)).

Example 5: Results

A bacterial-mammalian cell shuttle vector which replicates episomally in mammalian cells was constructed to express eIF-4E in HeLa cells (FIG. 1). Three separate plasmids were made containing the cDNAs for either unmodified eIF-4E$^{Ser}$ (RDB-wt), the variant eIF-4E$^{Ala}$ (RDB-Ala) or bacterial CAT (RDB-CAT, see FIG. 1).

HeLa cells transformed with the RDB-wt and RDB-Ala vectors were followed over time. After four days of G418 selection, untransformed cells had died and small colonies of resistant cells formed in the case of both vectors. Eleven days after selection, RDB-Ala-transfected cells had grown to small colonies with morphology indistinguishable from that of untransfected HeLa cells, i.e., flat, spindle-shaped, and with only a small proportion of round, dividing cells. In contrast, most of the RDB-wt-transfected cells were refractile, suggesting they were rounded-up and undergoing cell division. They also grew in foci which were larger than the RDB-Ala colonies and were many cells thick. After one month, the RDB-Ala-transfected cells had formed a confluent monolayer, but most of the RDB-wt-transformed cells had lysed. Those remaining were of unusual morphology. Closer examination of RDB-Wt-transfected cells two days earlier reveals large strangely shaped cells many of which contain multiple nuclei. In some cells, as many as 10 nuclei can be distinguished.

This experiment was performed a total of nine times, yielding similar results. In each instance, untransfected HeLa and RDB-Ala-transfected cells exhibited indistinguishable growth and morphology characteristics. RDB-Wt transfection, on the other hand, consistently resulted in rapidly growing foci which degenerated into syncytia, most of which died after one month. Attempts to preserve these cells by varying the selection protocol have prolonged their survival but never resulted in a stable cell line. Hela cell death is attributed to the fact that the Hela cell metabolic system was overwhelmed by an excess over expression of eIF-4E. However, it was experimentally found that the RDB vector replicates with a low copy-number in other cell lines from other species such as Th2 mouse cells and CHO hamster cells and that the overexpressed protein of interest could be obtained from these cells.

In these experiments, cells first appeared in G418-resistant colonies, and with time these developed into densely packed foci. It was of interest to test whether the foci would develop without G418 selection to rule out the possibility that they were artifacts of the transfection and selection protocol. Cells were transfected with RDB-Wt and then allowed to grow without G418. Foci were again observed, and at the same frequency as in the experiments where G418 selection was imposed.

The growth of an individual focus of cells was checked at 7, 10 and 15 days in the absence of selection. The contrast between refractile, rounded-up cells in the focus and the lawn of normal cells in monolayer was apparent. When G418 was added at 20 days, the lawn of cells died but those of the focus were completely resistant. Many of these cells also appeared to be multinucleated. All of the cells in the focus died by day 30, as observed in the previous experiments. These results indicate that the foci do not arise spontaneously; all of the normally growing cells in the lawn are untransfected whereas all of the rapidly growing cells in the focus are transformed with RDB-Wt. The formation of the multilayered foci amidst a monolayer of untransformed cells indicates that the cells in the foci are not contact inhibited. Untransfected HeLa cells were strongly contact inhibited and became arrested at confluence.

These results show that the abnormal growth phenotype is caused by the overexpression of a functional eIF-4E protein by the RDB-Wt vector. The G418-resistant cells obtained with the RDB-0 vector (no inserted cDNA), RDB-CAT (see FIG. 1) or RDB-Ala did not exhibit these effects, ruling out the possibility that the phenotype could be caused by the vector alone. The eIF-4E$^{Ala}$ protein expressed by RDB-Ala differs by only one amino acid from the wild type protein produced by RDB-Wt. This amino acid substitution (Ser to Ala) does not affect cap binding but renders the protein incapable of binding to the 48S initiation complex in an in vitro assay (Joshi-Barve, S., et al., *J. Biol. Chem.*, 265, 2979–2983 (1990)). It is interesting that overexpression of the eIF-4E$^{Ala}$ protein does not appear to interfere with mRNA translation by competition with the endogenous protein for cap binding.

Estimation of the eIF-4E level in RDB-Wt-transformed cells is problematical because the cells die after 30 days; the number of cells in the foci from even several flasks is still insufficient to perform accurate eIF-4E quantitations. Two approaches were taken to circumvent this problem. In the first, CAT activity was measured in RDB-CAT-transformed cells selected in an identical fashion to the RDB-Wt-transformed cells. The results are shown in Table 1 below.

TABLE 1

| Level of CAT expression in RDB-CAT-transformed cells | | | | |
|---|---|---|---|---|
| Sample | % Chloramp. acetylated % | CAT In assay ng | Volume of $10^6$ cells µl | [CAT] in cells nM |
| Bacterial CAT | 1.3 | 3 | | |
| | 4.3 | 15 | | |
| | 13 | 57 | | |

TABLE 1-continued

| Level of CAT expression in RDB-CAT-transformed cells | | | | |
|---|---|---|---|---|
| Sample | % Chloramp. acetylated % | CAT In assay ng | Volume of $10^6$ cells µl | [CAT] in cells nM |
| | 34 | 225 | | |
| | 53 | 900 | | |
| RDB-CAT Cells | 5.4 | 20 | 30 | 27 |

CAT assays were carried out in 0.1 ml reactions with [1,2-$^{14}$C] chloramphenicol (10 µM; $10^5$ cpm) and 10 mM acetyl coenzyme A (21). Cell extract from $10^6$ RDB-CAT-transformed cells were used in these assays, and reactions were carried out for 1 hr. Standards for CAT activity (purified bacterial enzyme) were purchased from Boehringer Mannheim (Indianapolis, IN). Acetylated products, which were separated by chromatography and counted, are expressed as percentage of input radioactivity.

Comparison with purified enzyme standards indicate that the cellular concentration of CAT was approximately 27 nM. Previously, it was estimated by immunological methods that the concentration of eIF-4E in rabbit reticulocytes was 8 nM (Hiremath, L. S. et al., *J. Biol. Chem.* 260, 7843–7849 (1985)). Thus, assuming that RDB vector-encoded CAT and eIF-4E, both of which are 25 kDa, accumulate to the same level, and that the endogenous eIF-4E concentration in HeLa cells and rabbit reticulocytes is the same, then it follows that the degree of overexpression was 3-fold.

The second approach was to measure the eIF-4E$^{Ala}$ content of the RDB-Ala-transformed cells, which grow continuously and can yield sufficient material for analysis. Cytoplasmic extracts were made from untransfected HeLa and RDB-Ala-transformed cells and the eIF-4E was enriched by affinity chromatography on m$^7$GTP-Sepharose. Bound protein was subjected to sodium dodecyl sulfate polyacrylamide gel electrophoresis (SDS-PAGE) and stained with Commissa Blue (FIG. 2).

The total amount of protein from the two lines exhibited the same pattern, but affinity-purified protein from RDB-Ala-transformed cells contained both more eIF-4E and more p220, a component of the eIF-4F complex (Rhoads, R. E., *Trends Biochem. Sci.* 13, 52–56 (1988); Sonenberg, N., *Prog. Nucl. Acid Res. Mol Biol.* 35, 173–207 (1988)).

Densitometry of the eIF-4E bands indicated that RDB-Ala-transformed cells contained 6-fold more eIF-4E than untransformed HeLa. Considering both methods of quantitation, the level of overexpression is estimated to be 3- to 6-fold.

To confirm that many different proteins can be overexpressed using the eIF-4E hybrid vector of the invention or modified vectors thereof, proteins such as neomycin, interleukin-2, bFGF, c-myc and were overexpressed. In the case of neomycin, the protein represented a second protein on the RDB-Wt vector or BK-4E modified vector and was overexpressed. In the case of bFGF and c-myc the proteins were endogenous to the cell line transfected with the RDB-WT vector, and bFGF and c-myc were overexpressed. In the case of interleukin-2, a plasmid carrying the interleukin-2 protein was co-transfected with the RDB-WT vector into murine Th1 and Th2 cell clones and interleukin-2 was overexpressed.

Overexpression of neomycin protein and T/t-Ag protein

Evidence of the overexpression of neomycin protein and T/t-Ag protein when incorporated in RDB vector and modified vector BK-4E follow.

FIG. 15 demonstrates the effect of overexpressing eIF-4E and two additional proteins which are operationally linked to the BK-4E or RDB vector of the present invention, which includes eIF-4E cDNA. FIG. 15 is an electrophoretic gel which clearly shows that both the T-Ag and the neo (aminoglycoside phosphotransferase) proteins are included and expressed from the RDB vector. These are easily identifiable proteins, since the vector is quite powerful even without eIF-4E. The proteins were characterized immunologically (not shown). These proteins are labelled in FIG. 15 with arrows, while the elevated, non-vector bands are marked with arrowless lines.

The effect of eIF-4E in overexpressing BK virus T-antigen (T-Ag) and neomycin (neo) proteins when operationally linked thereto is very clear from FIG. 15. Cells expressing a non-functional eIF-4E mutant express moderate levels of T-Ag and neo; whereas cells overexpressing the functional (Wt) eIF-4E express clearly more T-Ag and very high levels of neo protein. The effect is prominent for the neo protein because it is a bacterial gene with a poor translation context (5'UTR) with respect to eukaryotic systems. The amount of neo overexpressed in this experiment was 35 fold greater in CHO-4E cells (CHO cells transfected with the RDB or BK-4E vectors), and 100 fold greater after addition of TCDD (+) which induces maximal expression of eIF-4E.

The methodology for overexpression of interleukin-2 using eIF-4E follows.

Overexpression of IL-2 in TH1/TH2 Cells by co-transfection of lacZ and eIF-4E vector The regulation of a human IL-2 enhancer/Escherichia coli lacZ construct (hIL-2/lacZ), in murine Th1 and Th2 cell clones, was used to test the hypothesis that the inability of activated Th2 cells to express IL-2 was a consequence of inadequate levels of transcription factors. Activation of transfected T cells induced the hIL-2/lacZ construct in Th1 but not TH2 cells. However, hIL-2/lacZ was induced in activated Th2 cells that were cotransfected with a vector which overexpressed eukaryotic initiation factor 4E(eIF-4E), suggesting that the inability of Th2 cells to express IL-2 was due to a deficiency in the level of transcription factors.

This was confirmed by demonstrating that transcriptionally active levels of the DNA binding protein, NF-AT, occurred only in Th2 cells overexpressing eIF-4E but not in normal Th2 cells. These data suggest that concentrations of inducible transcription factors are a major component of the regulatory mechanisms dictating IL-2 expression and may be under translational control in Th1 /Th2 T cell subsets.

CD4⁺T helper/inducer (Th) cells, through their lymphokine secretion patterns, form a major regulatory component of the immune system. Differences in lymphokine production have been used to classify murine CD4⁺T cells into two functionally distinct subsets (Mosmann, T. et al., *J. Immunol.*, Volume 136 (1986) p. 348; Cherwinski, H. C. et al., *J. Exp. Med.*, Volume 166, (1987) p. 1229; and Mosmann, T. R. et al., *Ann. Rev. Immunol.*, Volume 7, (1989) p. 145); the Th1 subset, which is involved in delayed hypersensitivity and has been shown to synthesize interleukin-2 (IL-2), γ-interferon (IFN-γ)and lymphotoxin (LT), and the Th2 subset, which produces IL-4, IL-5, IL-6 and IL-10. Recent studies have suggested that a similar dichotomy also exists in human Th cell subsets (Ramagnani, S. Immunol. Today, Volume 12, (1991) p. 256; Del Prete, F. G. et al., *J. Clin. Invest.*, Volume 88, (1991) p. 346; Yamamura, M. et al., Science, Volume 254 (1991) p. 277; and Salgame, P. et al. Science, Volume 254, (1991) p. 279), however, the molecular basis for differential expression of lymphokine genes in T cells is not yet understood.

IL-2 is the major growth regulatory factor for T lymphocytes and its differential expression appears to be indicative of T cell differentiation and the type of immune effector function which develops in vivo. Expression of the human IL-2 gene is linked closely to T cell activation and is controlled by an enhancer element located between −319 and −52 bp 5' to the transcription initiation site of the gene (Fujita, T. et al. *Cell*, Volume 46, (1986) p. 401; Siebenlist, U. et al. Mol. Cell. Biol., Volume 6, (1986) p. 3042; Durand, D. B. et al. *J. Exp. Med.*, Volume 165, (1987) p. 395; Durand, D. B. et al. *Mol. Cell. Biol.*, Volume 8, (1988) p. 1715; and Crabtree, G. R. Science, Volume 243, (1989) p. 355).

The present inventors analyzed the regulation of the human IL-2 enhancer in murine Th1 and Th2 T cell clones, in response to receptor-mediated stimuli, as a model for determining the factors which control differential expression of IL-2. A reporter plasmid containing the human IL-2 enhancer-promoter element (−353 to +47) directing the transcription of the Escherichia coli lacZ (hIL-2/lacZ; FIG. 3A) was used to stably transfect murine Th1 and Th2 clones. The reported plasmid was made according to the method described in Crabtree, G. R. *Science*, Volume 243, (1989) p. 355 (incorporated herein by reference).

This reporter construct was prepared and used previously by Fiering et al. (Fiering, S. et al. *Genes. Dev.*, Volume 4, (1990) p. 1823) to study IL-2 enhancer function in the Jurkat T cells tumor line. The Th1 (S53) and Th2 (S053) clones used in this study were cloned from CD4+T cells isolated from C57BL/6 mouse spleen and exhibited distinct patterns of lymphokine expression, similar to those described for other Th1 and Th2 clones (Chang, J. C. C. et al., *J. Immunol.*, Volume 145, (1990) p. 409).

Stable hygromycin-resistant clones of Th1 and Th2 cells carrying the hIL-2/lacZ reporter construct were obtained. These stable transfectants were used initially to determine if the human IL-2 enhancer could also be differentially regulated in murine Th1 and Th2 T cell subsets. Unstimulated and stimulated Th1 and Th2 clones, transfected with the hIL2/lacZ construct, were analyzed by flow cytometry for lacZ expression as a measure of human IL-2 enhancer activity. Activation, via either the T cell receptor with anti-CD3 or concanavalin A (ConA) or by a combination of phorbol myristate acetate (PMA) and ionomycin, induced β-galactosidase (β-gal) expression in Th1 cells but not in Th2 cells (FIG. 3B). lacZ mRNA was not detectable in activated Th2 cells nor in control unstimulated Th1 or Th2 clones.

Despite the inability of the Th2 cells to express the hIL-2/lacZ construct they expressed IL-4 mRNA suggesting that they responded normally to receptor mediated stimuli. β-gal activity was higher in the Th1 clone following PMA and ionomycin activation than after treatment with ConA or anti-CD3 (FIG. 3B). Furthermore, the magnitude of the response increased with increasing concentrations of ionomycin (with PMA at 10 ng/ml; FIG. 4).

These results demonstrated that the human IL-2 enhancer was inducible by T cell activation in Th1 but not in Th2 clones indicating that it could be differentially regulated in distinct subsets of the helper T-cell compartment. The extent of hIL-2/lacZ activity at the single cell level was found to be heterogeneous since cloned Th1 cells showed a bimodal distribution patter of β-gal expression.

Lack of expression in some cells could have been a consequence of insufficient concentrations of transcription factors, and hence a failure to achieve the required threshold for transcriptional induction, or due to inadequate stimulation at the membrane level. A similar bimodal distribution of β-gal expression has been observed in Jurkat cells under control of NF-At, NF-KB or the entire IL-2 enhancer element (Fiering, S. et al. *Genes. Dev.*, Volume 4, (1990) p. 1823).

By gel retardation assays it was shown that concentrations of NF-AT exceeding a critical threshold were required for lacZ expression (Fiering, S. et al. *Genes. Dev.*, Volume 4, (1990) p. 1823). These data suggested that the concentrations of inducible transcription factors influenced the ability and extent of activation of the IL-2 enhancer within Th1 cells and could account for the inability of stimulated Th2 clones to express the hIL-2/lacZ construct. However, the presence of a negative regulatory factor could also play a role (Nolan, G. P. et al. *Proc. Natl. Acad. Sci. USA*, Volume 85, (1988) p. 2603; and Munoz, E. et al. Proc. Natl. Acad. Sci. USA, Volume 86, (1989) p. 9461).

It was observed that de novo synthesis of transcription factors is necessary for IL-2 transcription in resting cells (Crabtree, G. R. *Science*, Volume 243, (1989) p. 355), an increase in the translational capacity of Th2 cells could achieve the necessary thresholds to obtain IL-2 expression. The eukaryotic protein synthesis initiation factor 4E (eIF-4E) was overexpressed in Th2 (hIL-2/lacZ) transfectants.

Example 6: Overexpression of IL-2.

Overexpression of eIF-4E in the Th2 (hIL-2/lacZ) clone was accomplished by transfection with an episomally replicating mammalian expression vector containing eIF-4E cDNA (RDB vector) under the control of a 2,3,7,8-tetrachlorodibenzo-p-dioxin (TCDD)-inducible enhancer element (De Benedetti, A. et al. *Proc. Natl. Acad. Sci. USA*, Volume 87, (1990) p. 8212). Th2 cells containing the expression vector expressed 3-fold more eIF-4E than endogenous levels while treatment with TCDD resulted in 6–8 fold overall elevation.

eIF-4E at both basal and TCDD-induced concentrations was unable to activate the hIL-2 enhancer in unstimulated Th2 cells (FIG. 5). In contrast, activation of Th2 cells by PMA and ionomycin induced β-gal expression in the eIF-4E transfectants and the strength of induction was dependent on the level of expression of eIF-4E (FIG. 5). These data were consistent with the hypothesis that eIF-4E overexpression caused increased concentrations of the T-cell activation-dependent transcription factor(s) in Th2 cells, thus achieving the required concentrations for activation of the human IL-2 enhancer and resulting in overexpression of IL-2.

NF-AT activity is induced early after T cell activation and its DNA-binding activity is closely related to the activation of IL-2 transcription, and is dependent on de novo transcription and translation (Shaw, J. P. et al. *Science*, Volume 241 (1988) p. 202).

Inducible levels of transcriptionally active NF-AT in Th1 and Th2 clones were analyzed. A construct containing three tandem copies of a 30-bp NF-AT binding site linked to a minimal promoter, driving expression of lacZ (NF-AT/lacZ; Fiering, S. et al. *Genes. Dev.*, Volume 4, (1990) p. 1823), was used to detect transcriptionally active levels of NF-AT in Th1 and Th2 cells (FIG. 6A). This NF-AT trimeric binding site has been shown to act as a transcriptional enhancer solely responsive to transcriptionally active NF-AT (Fiering, S. et al. *Genes. Dev.*, Volume 4, (1990) p. 1823). Th1 and Th2 cell lines consisting of the integrated NF-AT/lacZ construct were generated as described above for the Th1 and Th2 (hIL-2/lacZ) cell lines.

Activation of Th1 cells caused induction of lacZ expression, consistent with NF-AT-dependent transcription; however, Th2 cells failed to do so (FIG. 6B). Using the identical NF-AT/lacZ construct in Jurkat cells, it has been shown that this construct requires a threshold of factor binding to achieve transcriptional function. Hence, failure of lacZ expression in Th2 cells appears to have resulted from a suboptimal concentration of transcriptionally active NF-AT.

In contrast, overexpression of eIF-4E in Th2 cells [Th2 (NF-AT/lacZ) (eIF-4E)] induced lacZ expression upon activation of the T cell receptor signaling pathway (FIG. 6B). These data evidence that eIF-4E raised the inducible NF-AT concentrations to levels that were sufficient to be transcriptionally active.

Alternatively, the effect of eIF-4E on β-gal expression in Th2 cells could have been due to a translational enhancement of a low basal level of lacZ mRNA. To rule out this possibility the level of lacZ mRNA was examined in Th1 (NF-AT/lacZ) as well as Th2 (NF-AT/lacZ) and Th2 (NF-AT/lacZ; eIF-4E) cells by an RNases protection assay. Stimulation by PMA and ionomycin induced lacZ transcription in Th1 (NF-AT/lacZ) cells as expected. However, PMA and ionomycin activation was unable to induce lacZ transcription in Th2 (NF-AT/lacZ) cells in the absence of eIF-4E, whereas overexpression of eIF-4E resulted in the induction lacZ message, and thus overexpression of IL-2 (FIG. 6C). Increased eIF-4E activity has been suggested to enhance specific translation of weak mRNAs, many of which are protooncogenes, housekeeping genes and differentiation factors (Thach, R. E. *Cell*, Volume 68 (1992) p. 177). The present data suggest that there may be a translational control of the NF-AT complex that in turn affects the transcription of IL-2 in the Th2 subset.

In conclusion, the activation of the human IL-2 enhancer and the NF-AT controlled enhancer were differentially regulated in murine Th1 and Th2 clones. T cell activation-dependent expression occurred only in transfected Th1 cells. However, when Th2 cells were co-transfected with eIF-4E, activation dependent expression of the human IL-2 enhancer and NF-AT controlled enhancer also occurred.

Thus, overexpression of eIF-4E, a rate-limiting factor in protein synthesis, was able to effect activation dependent transcription from constructs controlled by multiple distinct inducible factors (hIL-2/lacZ) or a single inducible factor (NF-AT/lacZ). These data support the dichotomy in IL-2 expression in T helper subsets results from inherent differences in the concentrations of the regulatory factor(s) in general and NF-AT in particular and that similar regulatory mechanisms may be operative in human Th cells.

FIG. 3(A) shows a map of the human IL-2 enhancer-promoter/lacZ reporter construct used to transfect Th1 and Th2 clones. This includes the entire enhancer from −52 to −319. Sites that have been identified to bind proteins and are believed to contribute to transcriptional activation are noted (Fiering, S. et al. *Genes. Dev.*, Volume 4, (1990) p. 1823; Shaw, J. P. et al. *Science*, Volume 241 (1988) p. 202). Escherichia coli lacZ is attached to the IL-2 gene at position +47 and does not include the translational start site of IL-2. The promoter is located from −70 to +47 and includes a TATA box.

FIG. 3(B) shows analysis of lacZ expression directed by the human IL-2 enhancer in hIL-2/lacZ transfected murine Th1 and Th2 clones. The Th1 (S53) and the Th2 (S053) clones were stably transfected with the hIL-2/lacZ reporter construct (Fiering, S. et al. *Genes. Dev.*, Volume 4, (1990) p.

1823) by the calcium phosphate method (Sambrook, J. et al. Molecular Cloning: A Laboratory Manual (Cold Spring Harbor Laboratory, New York, 1989)). Th1 and Th2 (hIL-2/lacZ) clones were activated using Con A (5 µg/ml), anti-CD3 (αCD3 plate bound) or PMA (10 ng/ml) and 2.25 µM ionomycin (PMA+Iono) as shown in the figure; unstimulated cells (US) that did not receive any treatment were used as a control. All cells were harvested 18 hours after simulation and stained for β-gal expression with fluorescein-β-D-galactopyranoside (FDG), by the method of Nolan et al. (Nolan, G. P. et al. Proc. Natl. Acad. Sci. USA, Volume 85, (1988) p. 2603) as recommended by the manufacturer (Molecular Probes, Inc.). Cells were analyzed with a fluorescence activated cell sorter (FACS) analyzer (Becton Dickinson). The percentage of cells which were positive for β-gal were; Th2, US—5%, TH2, PMA+Iono—6%; TH1, US—6%, TH1, ConA—17%; TH1, αCD3—27%; TH1, PMA+Iono −43%. (Not shown: TH2, ConA—5%; TH2, αCD3—6%).

FIG. 4 shows analysis of the effect of ionomycin concentration on β-gal activity in a Th1 clone transfected with the hIL-2/lacZ construct. Cells were stimulated with 10 ng/ml PMA and varying concentrations of ionomycin (0.5 to 2.25 µM), harvested 18 hours after stimulation and β-gal expression analyzed as described in FIG. 3B. The percentage of β-gal$^+$ cells at each concentration of ionomycin were: unstimulated control (US)—7%; 0.5 µM −23%; 1.0 µM −32%; 1.5 µM −37%; 2.25 µM −43%.

FIG. 5 shows analysis of the effect of eIF-4E on hIL-2/lacZ expression in Th2 cells. Th2 cells transfected with hIL-2/lacZ were further transfected with eIF-4E (De Benedetti, A. et al. Proc. Natl. Acad. Sci. USA, Volume 87, (1990) p. 8212), selected and maintained using G418 (500 µg/ml). Experimental treatments were as follows: US—Unstimulated Control; TCDD (50 nM), to induce the eIF-4E construct; PMA+Ionon—PMA (10 ng/ml) and ionomycin (2.25 µM); TCDD+PMA+Iono—TCDD (50 nM), PMA (10 ng/ml) and ionomycin (2.25 µM). Cells were harvested 18 hours after treatment and β-gal expression was analyzed as described in FIG. 3. The percentage of cells which expressed β-gal were: UT −6%; TCDD −7%; PMA+Iono −21%; TCDD+PMA+Iono −29%.

FIG. 6(A) shows a map of the NF-AT/lacZ reporter construct used to transfect Th1 and Th2 clones (Fiering, S. et al. Genes. Dev., Volume 4, (1990) p. 1823).

FIGS. 6(B,C,D) shows analysis of the effect of eIF-4E on NF-AT/lacZ expression in Th2 cells. Different experimental treatments were as follows: US—Unstimulated control FIG. 6(B); PMA+Iono—PMA (10 ng/ml) [FIG. 6C] and ionomycin (2.25 µM [FIG. 6D]). Cells were harvested at 18 hours and β-gal expression analyzed as described in FIG. 3, to monitor NFAT-dependent lacZ expression. The percentage of cells which expressed β-gal is indicated in parenthesis.

FIG. 6E shows determination of the chimeric IL-2/lacZ mRNA from the NF-AT/lacZ construct by the RNase protection assay. A 320 nt minus-sense 3H-labeled RNA was prepared form PstI-digested pSP65Gal (Fiering, S. et al. Genes. Dev., Volume 4, (1990) p. 1823).

RNA isolation and RNase protection was performed as described earlier; the samples were separated on a 8% polyacrylamide denaturing gel. Lanes D and P represent the digested and undigested probe, respectively. Th1 and Th2 clones transfected with the NF-AT/lacZ construct are indicated. Th2 (NF-AT/lacZ) transfected with eIF-4E are indicated with (+). The transfected cells were stimulated with PMA (10 ng/ml) and ionomycin (2.25 µM), as indicated. The arrow shows a 250 nt-protected fragment, as expected from a properly initiated IL-2 transcriptional initiation start site.

Functions of eIF-4E

EIF-4E is a 25-kDa phosphoprotein which specifically binds to the 7-methylguanosine-containing cap of mRNA—the first step of mRNA recruitment for translation. EIF-4E is also one component of the three-subunit initiation factor complex eIF-4E, which promotes the unwinding of secondary structure in the 5' untranslated region *UTR) of mRNA. The activity of eIF-4E is modulated by phosphorylation at is Ser-53 residue. A variety of mitogens induced phosphorylation of eIF-4E and concomitantly increase protein synthesis rates. Conversely, quiescent cells contain mostly unphosphorylated. The low abundance of phosphorylated eIF-4E creates a situation of competition among different mRNA species, such that mRNAs with long and highly structure 5' UTRs are apparently outcompeted for binding to ribosomes by the "strong" mRNAs. An analysis of sequence data from 699 vertebrate mRNAs showed that more than 90% of them contain 5' UTRs that are less than 200 nucleotides long and devoid of upstream AUGs, which is characteristic of many "strong" mRNAs. A clear exception to this paradigm are the mRNAs coding for many oncogenes and growth factors, which posses long G+C-rich 5' UTRs and, frequently, upstream AUGs, suggesting that the expression of these genes is subject to translational regulation.

In line with these observations, it was demonstrated that overexpression of eIF-4E specifically increases the translation of model mRNAs containing excessive secondary structure in their 5' UTR. In addition, overexpression of eIF-4E (but not of the eIF-4E/Ala-53 variant) causes malignant transformation and deregulated growth of rodent and human cells. EIF-4E also acts as a potent enhancer of transformation in cooperation with v-myc or E1A.

Conversely, it was demonstrated that reducing the level of eIF-4E with antisense RNA inhibited the oncogenic and metastatic properties of T24H-ras-transformed CREF cells. Finally, eIF-4E apparently controls the state of cellular differentiation in some systems, as demonstrated for PC12 cells treated with NGF and in regenerating liver. Overexpression of eIF-4E alters the pattern of lymphokine expression and the activity of NF-AT (a T-cell-specific transcription factor) in differentiated Th2 lymphocytes.

The central idea that even a modest increase in translation rates can have a major impact on the expression of translationally-controlled (or repressed) mRNAs.

The present inventors use cells overexpressing eIF-4E as a means to identify these transcripts, and to try to understand how their overexpression leads to neoplastic transformation. This approach is different from current studies on oncogenesis aimed at identifying genes at the boundaries of cytogenetic translocations and deletions. These rearrangements certainly occur in several neoplastic predispositions, and have greatly helped in our understanding of cancer as a genetic disorder.

BK-virus based episomal vector:

A convenient vector for the expression of genes in mammalian cells has been developed. This vector was progressively refined to include a very specific (dioxin-inducible) promoter, a multiple cloning site (MCS) and trimmed in size in non-essential regions. An important property of this vector is the fact that it remains in unintegrated form after transfection into mammalian cells, i.e. it can be shuttled back and forth from bacteria to mammalian cells. Since the BK virus T-antigen (necessary for vector replication) is efficiently expressed, the host range of transforamtion is very broad. For example, the vector is maintained episomally at high copy number in HeLa, HOS, COS, CHO, CREF, NIH3T3, dog-pancreas, and Th lymphocytes.

This is clear advantage in comparison to similar vectors containing an SV40-origin, and require transfection into (SV40) T-Ag-expressing cells (e.g., COS7) which greatly limits the experimental flexibility. Therefore, this vector is ideally suited for expression/cloning of mammalian genes. The vector promoter is composed of the MMTV promoter, controlled by the enhancer of Cyt-P450, which is inducible by dioxins—very specific inducer, unlike the promiscuous inducers commonly used for mammalian cells. The MCS contains three rare eight-base cutter (Notl, Srfl and Pacl), which simplifies the protocol for the construction of directional cDNA libraries. In the past, an earlier design of this vector has also been our main vehicle to overexpress eIF-4E.

Although the vector resulted in excessive over-production of eIF-4E which proved to be lethal in several cell lines, the addition of a spacer (about 80 nt of extended 5' UTR) in front of the eIF-4E cDNA was sufficient to contain the level of overexpressed eIF-4E to 3–5-fold (see FIG. 14). This level of expression is sufficient to neoplastically transform cells, without being lethal. When higher levels of overexpression are needed, the addition of tetrachloro-dibenzo-dioxin (TCDD) to the medium can further raise the level about 10-fold.

eIF-4E overexpression in HeLa cells:

The effect of eIF-4E overexpression in HeLa using the RDB vector was studied. Soon after transfection, the cells overexpressing eIF-4E display a marked stimulation of proliferation and shortening (20% reduction) of average generation time, and they form densely packed foci. Later on, the cells become multinucleated, failed to undergo cytokinesis, and ultimately lyse about one month after transfection.

Transfection with an identical construct, but for one changed residue in eIF-4E (Ala in place of Ser at position 53, i.e. non-phosphorylatable mutant) does not produce these effects. Unfortunately, because overexpression of eIF-4E (wt) has proved to be lethal in these cells, we were unable to obtain a line of stably transfected cells.

With the modified RDB vector (BK-4E) with spacer mentioned above, a line of stably transformed HeLa cells was obtained. These cells grow as a persistent mixture of two populations: one composed of rapidly dividing cells, the other represented by gigantic multinucleated cells (FIG. 7), which frequently fuse to form syncytia (top left frame).

FIG. 8 shows the multinucleation phenomenon in greater details. Here a single cell, stained with propidium-iodide (chormatin-dye), is viewed by confocal microscopy. At least either nuclei can be identified, each containing heterogeneous amounts of chromatin, suggestive of aberrant mitotic segregation. This effect is probably due to a loss of synchronicity between accelerated round of mitosis and cytokinesis. Addition of TCDD to the medium (to induce maximal levels of eIF-4E) results in a nearly complete conversion of HeLa-4E cells to the multinucleated phenotype. This process lasts approximately one week before cell lysis, which give us ample time to study many morphologic and biochemical changes.

HeLa-4E cells constitute one of the best available models to study mechanisms of apoptosis and aberrant chromosome segregation, because of the possibility of inducing these processes with TCDD.

Several recent reports indicate that overexpression of protooncogenes is frequently cytopathic, and can lead to apoptosis. This was shown for c-myc, mos, and T24 H-ras plus PKC.

Overexpression of eIF-4E produces similar effects by upregulating one or more of these gene products, but we do not known the exact sequence of events, nor if the early and late effects involve the same factors. It is not known if the increased proliferation and aberrant mitoses are a manifestation of the same basic dysfunction, or the result of distinct determinants.

Regardless of the mechanism, the multinucleated phenotype and segregation defects provide a basis for our contention that changes in translation rates can ultimately result in chromosomal alterations, analogous to those typically found in later stages of cancer. Of course, this process will be enhanced by a genotypic selection for the most aggressive phenotype.

Overexpression of eIF-4E in CHO:

After working with eIF-4E overexpressing cells, it was suspected that it may be particularly difficult to obtain stable transformants from already tumorigenic cells. This has been the case for HeLa, human osteosarcomas (HOS), and mouse erythroleukemia cells. In contrast, the present inventors were able to transform continuous rat embryo fibroblasts (CREF), CHO and T-lymphocytes, all of which are non-tumorigenic. Most of the work utilized the CHO-4E cells which are normal mammalian cell lines.

Overexpression of eIF-4E in CHO cells results in a transformed phenotype which includes morphological changes, loss of contact inhibition, shortening of generation time, and growth in soft agar. [$^3$H]-thymidine-incorporation experiments with synchronized cells showed that, surprisingly, the phase of the cell-cycle which is shortened in CHO-4E is S. Neither G0+G1 or G2+M were appreciably shortened in these cells. Thus, it appears that CHO-4E cells can produce a greater number of DNA replication centers. None of these changes are observed in control cells which overexpress the non-phosphorylatable eIF-4E/Ala-53 variant, confirming the importance of Ser-53 for eIF-4E activity.

The basal level of overexpressed eIF-4E was 3.5-fold, and 10-fold after TCDD-induction, for both CHO-4E and CHO-4EAla cells (FIG. 9).

Whether the expression of c-myc was altered in these cells was investigated. The c-myc mRNA of vertebrates comprises three exons, the first of which is non-coding. This exon is missing in the retrovirally-transduced v-myc. It is postulated that this region of the gene is important for controlling c-myc expression since, in 70% of mouse plasmacytomas and in human lymphomas, the breakpoint in c-myc occurs in the first exon or intron. Moreover, the nucleotide sequence of exon 1 is highly conserved among species despite the fact that it is untranslated.

The long 5' UTR of c-myc mRNA (550 bases) contains several upstream AUG initiation-codons and multiple terminators in all three reading frames, which makes the c-myc mRNA unfit for the ribosome-scanning model, and a classic candidate for translational repression. The possibility that exon 1 could modulate the translational efficiency of c-myc mRNA was first postulated by Saito et al., who predicted the formation of a large hairpin structure between exons 1 and 2, which a ΔG of 70 kcal/mol. A region which is cis-inhibitory for in vitro translation was later assigned to regions in exon 1 for both the natural c-myc mRNA and in heterologous reporter constructs.

Overexpression of c-myc

Overexpression of eIF-4E in CHO (CHO-4E) cells leads to a specific (about 4-fold) increase in endogenous c-myc expression (FIG. 10). The specific increase in translation of the endogenous c-myc mRNA was studied using the RDB-WT vector of the present invention. This was obtained by elevating the translational capacity of these cells, and presumably reducing the competition among mRNAs. Both 62 kDA and 64 kDa myc polypeptides are elevated in CHO-4E, with a preferential increase of the 64 kDA. (62 kDA and 64 kDa myc polypeptides were obtained according to the method of Hann, S. R., Thompson, C. B. and Eisenman, R. N. (1985) "c-myc oncogene protein synthesis is independent of the cell cycle in human and arian cells" Nature, Vol 314, pp. 366–369; incorporated herein by reference. Since in most species the 64 kDa protein is the result of a non-AUG (i.e., CUG) translational initiation of the c-myc mRNA, this result suggests that eIF-4E may be directly involved in selection of the initiation site for translation.

Recent evidence implicates eIF-4 in AUG-initiation-codon selection on model bicistronic constructs, and its role in the preferential utilization of the most upstream AUG. This is the first in vivo indication that eIF-4E may preferentially elicit a non-AUG selection for translation initiation. Whether the 62 and 64 kDA MYC proteins play completely equivalent functions, or localize to the same targets, is presently unknown.

As mentioned above, the increase in c-myc expression is primarily translational. However, an unexpected finding of this work was a reversion in the level of P1 vs. P2-initiated c-myc transcripts in CHO-4E cells (FIG. 11. This is an important observation, since a similar shift in promoter utilization has been observed in several cases of Burkitt's lymphomas. Research strongly indicates that this shift depends on trans-acting factor, rather than on cis-acting elements and chromosomal position effects dictated by the translocation shuffle, as previously suggested.

No chromosomal rearrangements involving the myc gene likely occurred in CHO-4E cells, as confirmed by primer-extension data. This provides a model to study how alterations of the in vivo translation of a specific growth-control transcription factor (myc) may lead to changes of its own expression.

Overexpression of b-FGF

Overexpression of endogenous basic fibroblast growth factor (b-FGF) using the hybrid vector of the present invention was also studied. Immunoprecipitations and western-blot analyses of CHO vs. CHO-4E cells revealed a dramatic (>20-fold) increase in the expression of bFGF (FIG. 12). This analysis also showed that, at steady-state all four forms of bFGF were similarly increased (westerns), but immunoprecipitation analysis of newly synthesized bFGF by pulse-labeling (1 h) indicated that the most prominently increased form was the 21 kDA protein.

The 21 kDA protein is obtained by an alternate translation initiation pattern, beginning at codon CUG-1, 56aa upstream of the canonical AUG-codon. Since the bFGF mRNA is the same for all four proteins (in all animal species) this example clearly shows that the preferential synthesis of the 21 kDA in CHO-4E cells is at the level of translation.

Further confirmation of translational regulation came from northern analysis of the bFGF mRNA, since CHO and CHO-4E cells express the same level of FGF mRNA (not shown). Protein stability of the different forms probably plays a role in their relative accumulation, as indicated by western. Significant amounts of (metabolically-labeled) bFGF (0.5 mg/L) by heparin-sepharose chromatography from the medium of CHO-4E, but not from CHO cells were isolated. bFGF contributes to the highly transformed phenotype of CHO-4E cells.

Effects of the expression of antisense-RNA against eIF-4E:

Human and rodent cell lines which are moderately or completely (conditional lethals) deficient in eIF-4E were generated, by the use of antisense-RNA technology. The strongest eIF-4E reduction was obtained with our episomal expression vector, whereas intermediate levels of reduction were obtained with integrating constructs. In all these constructs, the promoter driving the antisense-RNA was inducible with TCDD to further reduce the level of eIF-4E. In HeLa cells the episomal vector which resulted in a slow-growth was utilized, and conditionally lethal phenotype. Translation rate in vivo and in cell-free systems were reduced in direct relationship with the level of eIF-4E. Both eIF-4E and eIF-4γ (the partner of eIF-4E) were concomitantly reduced. Protein synthesis patterns in these cells showed the translation of most mRNAs was inhibited. However, the synthesis of certain proteins in these cells showed that the translation of most mRNAs was inhibited. However, the synthesis of certain proteins appeared to be resistant to the loss of eIF-4E. It was determined that several of these "resistant" mRNAs encode heat shock proteins indicating that the translation of these, and a few additional unidentified mRNAs, may be "cap-independent" for translation.

eIF4E regulation of ras oncogene

Substantial knowledge on the interplay between the ras gene and eIF-4E has been gained. This was in large part due to the ability to reduce the level of eIF-4E in T24/H-ras-transformed CREF cells (tumorigenic in nude mice). The phosphorylation and activity of eIF-4E greatly increased in CREF cells transformed with T25/H-ras, and suggested that ras may mediate some of its neoplastic effects by elevating an eIF-4E kinase. Additional evidence shows by reducing the level of eIF-4E in these cells, T24/H-ras cells transfected with an integrated eIF-4E antisense-vector grow almost as fast as their parental cell. However, most of the tumorigenic properties of these cells were lost, and phenotypically they reversed to a flat morphology.

This indicates that important mediators of the RAS-oncogenic pathway involves translationally repressed mRNAs, which require elevated eIF-4E activity for their expression. The work also indicates that it is possible to reverse the oncogenic properties of a variety tumorigenic cells by targeting eIF-4E.

The invention now being fully described, it will be apparent to one of ordinary skill in the art that many changes and modifications can be made thereto without departing from the spirit or scope of the invention as set forth herein. All publications and methodology mentioned herein are incorporated by reference.

SEQUENCE LISTING ( 1 ) GENERAL INFORMATION:

( i i i ) NUMBER OF SEQUENCES: 1

( 2 ) INFORMATION FOR SEQ ID NO:1:

( i ) SEQUENCE CHARACTERISTICS:
( A ) LENGTH: 1897 base pairs
( B ) TYPE: nucleic acid
( C ) STRANDEDNESS: single
( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:1:

| | | | | | | |
|---|---|---|---|---|---|---|
| CGATCAGATC | GATCTAAGAT | GGCGACTGTC | GAACCGGAAA | CCACCCCTAC | TCCTAATCCC | 60 |
| CCGACTACAG | AAGAGGAGAA | AACGGAATCT | AATCAGGAGG | TTGCTAACCC | AGAACACTAT | 120 |
| ATTAAACATC | CCCTACAGAA | CAGATGGGCA | CTCTGGTTTT | TTAAAAATGA | TAAAAGCAAA | 180 |
| ACTTGGCAAG | CAAACCTGCG | GCTGATCTCC | AAGTTTGATA | CTGTTGAAGA | CTTTTGGGCT | 240 |
| CTGTACAACC | ATATCCAGTT | GTCTAGTAAT | TTAATGCCTG | GCTGTGACTA | CTCACTTTTT | 300 |
| AAGGATGGTA | TTGAGCCTAT | GTGGGAAGAT | GAGAAAAACA | ACCGGGGAGG | ACGATGGCTA | 360 |
| ATTACATTGA | ACAAACAGCA | GAGACGAAGT | GACCTCGATC | GCTTTTGGCT | AGAGACACTT | 420 |
| CTGTGCCTTA | TTGGAGAATC | TTTTGATGAC | TACAGTGATG | ATGTATGTGG | CGCTGTTGTT | 480 |
| AATGTTAGAG | CTAAGGTGA | TAAGATAGCA | ATATGGACTA | CTGAATGTGA | AACAGAGAA | 540 |
| GCTGTTACAC | ATATAGGGAG | GGTATACAAG | GAAAGGTTAG | CTTTCCTCC | AAAGATAGTG | 600 |
| ATTGGTTATC | AGTCCCACGC | AGACACAGCT | ACTAAGAGCG | GCTCCACCAC | TAAAAATAGG | 660 |
| TTTGTTGTTT | AAGAAGACAC | CTTCTGAGTA | TTCTCATAGG | AGACTGCGTC | AAGCAATCGA | 720 |
| GATTGGGAG | CTGAACCAAA | GCCTCTTCAA | AAAGCAGAGT | GGACTGCATT | TAAATTTGAT | 780 |
| TTCCATCTTA | ATGTTACTCA | GAGTATAAGA | GAAGTCTCAT | TCGCCTTTGT | CTTGTACTTC | 840 |
| TGTGTTCATT | TTTTTTTTT | TTTTTGGCT | AGAGTTTCCA | CTATCCCAAT | CAAAGAATTA | 900 |
| CAGTACACAT | CCCCAGAATC | CATAAATGTG | TTCCTGGCCC | ACTCTGTAAT | AGTTCAGTAG | 960 |
| AATTACCATT | AATTACATAC | AGATTTTACC | TATCCACAAT | AGTCAGAAAA | CAACTTGGCA | 1020 |
| TTTCTATACT | TTACAGGAAA | AAAAATTCTG | TTGTTCCATT | TTATGCAGAA | GCATATTTTG | 1080 |
| CTGGTTTGAA | AGATTATGAT | GCATACAGTT | TTCTAGCAAT | TTCTTTGTT | TCTTTTTACA | 1140 |
| GCATTGTCTT | TGCTGTACTC | TTGCTGATGG | CTGCTAGATT | TTAATTTATT | TGTTTCCCTA | 1200 |
| CTTGATAATA | TTAGTGATTC | TGATTTCAGT | TTTTCATTTG | TTTTGCTTAA | ATTTTTTTT | 1260 |
| TTTTTTTCCT | CATGTAACAT | TGGTGAAGGA | TCCAGGAATA | TGACACAAAG | GTGGAATAAA | 1320 |
| CATTAATTTT | GTGCATTCTT | TGGTAATTTT | TTTGTTTT | TGTAACTACA | AAGCTTTGCT | 1380 |
| ACAAATTTAT | GCATTTCATT | CAAATCAGTG | ATCTATGTTT | GTGTGATTTC | CTAAACATAA | 1440 |
| TTGTGGATTA | TAAAAAATGT | AACATCATAA | TTACATTCCT | AACTAGAATT | AGTATGTCTG | 1500 |
| TTTTTGTATC | TTTATGCTGT | ATTTTAACAC | TTTGTATTAC | TTAGGTTATT | TGCTTTGGT | 1560 |
| TAAAAATGGC | TCAAGTAGAA | AAGCAGTCCC | ATTCATATTA | AGACAGTGTA | CAAAACTGTA | 1620 |
| AATAAAATGT | GTACAGTGAA | TTGTCTTTTA | GACAACTAGA | TTTGTCCTTT | TATTTCTCCA | 1680 |

| | | | | | |
|---|---|---|---|---|---|
| TCTTTATAGA | AGGAATTTGT | ACTTCTTATT | GCAGGCAAGT | CTCTATATTA | TGTCCTCTTT | 1740 |
| TGTGGTGTCT | TCCATGTGAA | CAGCATAAGT | TTGGAGCACT | AGTTTGATTA | TTATGTTTAT | 1800 |
| TACAATTTTT | AATAAATTGA | ATAGGTAGTA | TCATATATAT | GGAAAAAAAA | AAAAAAAAA | 1860 |
| AAAAAAAAAA | AAAAAAAAA | AAAAAAAAA | AAAAAA | | | 1897 |

We claim:

1. A hybrid vector consisting of a replicating vector comprising first and second DNA segments, said first DNA segment encoding a cap-binding protein which binds to the cap structure of translationally repressed mRNA and mediates ribosome-binding, said cap-binding protein consisting of eukaryotic protein synthesis initiation factor 4E, eIF-4E factor, or a mutant thereof which maintains eIF-4E cap binding function, and said second DNA segment encoding a polypeptide or protein which is expressed, wherein said polypeptide or protein encoded by said second DNA segment is expressed at a level higher than the level of expression thereof in the absence of said first DNA segment.

2. The hybrid vector of claim 1, wherein the vector is the vector BK-4E deposited as ATCC Accession No. 98045 or RDB-WT deposited as Accession No. 98046.

3. The hybrid vector of claim 1, further comprising a spacer of about 80 nucleotides inserted in front of said first DNA segment.

4. The hybrid vector of claim 1, comprising multiple copies of the first DNA segment.

5. The hybrid vector of claim 1 comprising multiple copies of the second DNA segment.

6. A eukaryotic host cell transformed with the hybrid vector of claim 1.

7. A method of increasing the expression of a polypeptide or protein in a eukaryotic host cell, comprising transforming a eukaryotic host cell which expresses said polypeptide or protein with a replicating hybrid vector comprising a DNA segment encoding a gap-binding protein which binds to the cap structure of translationally repressed mRNA and mediates ribosome-binding, said cap-binding protein consisting of eIF-4E factor or a mutant thereof which maintains eIF-4E cap binding function; and culturing the transformed cell in an expression medium whereby said cap-binding protein and said polypeptide or protein are expressed at a level higher than that without the hybrid vector.

8. The method of claim 7, wherein said polypeptide or protein is encoded in the genome of the host cell.

9. The method of claim 7, wherein said polypeptide or protein is encoded in extragenomic DNA.

10. The method of claim 7, wherein said polypeptide or protein is encoded by a second hybrid vector.

11. The method of claim 7, wherein said polypeptide or protein is encoded by a second DNA segment operatively linked to the hybrid vector.

12. The method of claim 7, wherein said polypeptide or protein is produced at a level at least about 1.1 times the level of expression thereof in the absence of said DNA segment encoding a cap-binding protein.

13. A hybrid vector according to claim 1, wherein said polypeptide or protein is selected from the group consisting of chloramphenicol acetyl transferase, neomycin phosphotransferase, insulin, interferon, growth hormone, basic fibroblast growth factor, proteins encoded by oncogenes, tissue plasminogen activator, hepatitis B vaccine proteins, endorphins, and interleukins.

14. A hybrid vector according to claim 13 wherein said polypeptide or protein is neomycin phosphotransferase.

15. A host cell according to claim 6, wherein said host cell is selected from the group consisting of Hela cells, Chinese Hamster Ovary (CHO) cells, CREF cells, human osteosarcoma (HOS) cells and T lymphocytes.

* * * * *

UNITED STATES PATENT AND TRADEMARK OFFICE
CERTIFICATE OF CORRECTION

PATENT NO. : 5,646,009
DATED : July 8, 1997
INVENTOR(S) : Robert E. RHOADS et al.

It is certified that error appears in the above-identified patent and that said Letters Patent is hereby corrected as shown below:

On the title page, item [75] should read as follows:

--[75] Inventors: Robert E. Rhoads; Arrigo De Benedetti, both of Shreveport, LA--

Signed and Sealed this

Twenty-seventh Day of January, 1998

Attest:

Attesting Officer

BRUCE LEHMAN

Commissioner of Patents and Trademarks